US010279148B2

(12) United States Patent
Rosenberg et al.

(10) Patent No.: US 10,279,148 B2
(45) Date of Patent: *May 7, 2019

(54) SYSTEMS AND METHODS FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/704,177

(22) Filed: Sep. 14, 2017

(65) Prior Publication Data

US 2018/0001059 A1 Jan. 4, 2018

Related U.S. Application Data

(60) Continuation of application No. 15/384,910, filed on Dec. 20, 2016, now Pat. No. 9,789,288, which is a division of application No. 13/713,239, filed on Dec. 13, 2012, now Pat. No. 9,550,043.

(51) Int. Cl.
*A61M 25/04* (2006.01)
*A61M 25/02* (2006.01)

(52) U.S. Cl.
CPC ............ *A61M 25/04* (2013.01); *A61M 25/02* (2013.01); *A61M 2025/028* (2013.01); *A61M 2025/0286* (2013.01)

(58) Field of Classification Search
CPC .............. A61M 525/04; A61M 525/02; A61M 2025/028; A61M 2025/0286
See application file for complete search history.

(56) References Cited

U.S. PATENT DOCUMENTS

| | | |
|---|---|---|
| 2,525,398 A | 10/1950 | Collins |
| 3,039,468 A | 6/1962 | Price |
| 3,059,645 A | 10/1962 | Hasbrouck et al. |
| 3,108,595 A | 10/1963 | Overment |
| 3,176,690 A | 4/1965 | H'doubler |
| 3,308,819 A | 3/1967 | Arp |
| 3,630,195 A | 12/1971 | Santomieri |
| 3,677,250 A | 7/1972 | Thomas |

(Continued)

FOREIGN PATENT DOCUMENTS

| | | |
|---|---|---|
| WO | WO 1991/15254 | 10/1991 |
| WO | WO 1998/10823 | 3/1998 |

(Continued)

OTHER PUBLICATIONS

European Search Report, Application No. 13863190.8, dated Aug. 16, 2016, 4 pages.

(Continued)

*Primary Examiner* — Imani N Hayman
*Assistant Examiner* — Tiffany Legette
(74) *Attorney, Agent, or Firm* — Fish & Richardson P.C.

(57) ABSTRACT

Some embodiments of a medical device anchor system include an anchor device that secures a medical instrument (such as a catheter or the like) in place relative to a skin penetration point using subcutaneous anchors.

20 Claims, 14 Drawing Sheets

(56) References Cited

U.S. PATENT DOCUMENTS

| | | |
|---|---|---|
| 3,717,151 A | 2/1973 | Collett |
| 3,765,032 A | 10/1973 | Palma |
| 3,825,010 A | 7/1974 | McDonald |
| 3,834,380 A | 9/1974 | Boyd |
| 3,856,009 A | 12/1974 | Winnie |
| 3,896,527 A | 7/1975 | Miller et al. |
| 3,938,529 A | 2/1976 | Gibbons |
| 4,043,346 A | 8/1977 | Mobley et al. |
| 4,114,618 A | 9/1978 | Vargas |
| 4,164,943 A | 8/1979 | Hill et al. |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,368,017 A | 11/1994 | Sorenson et al. |
| 5,378,239 A | 1/1995 | Termin et al. |
| 5,456,671 A | 10/1995 | Bierman |
| 5,496,277 A | 3/1996 | Termin et al. |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,265 A | 11/1999 | Bouquet De La Joliniere et al. |
| 6,213,979 B1 | 4/2001 | Bierman |
| 6,231,548 B1 | 5/2001 | Bassett |
| 6,290,676 B1 | 9/2001 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,896,665 B2 | 5/2005 | Picha et al. |
| 6,958,044 B2 | 10/2005 | Burbank et al. |
| 7,056,286 B2 | 6/2006 | Ravenscroft et al. |
| 2001/0056261 A1 | 12/2001 | Lerman et al. |
| 2002/0068898 A1 | 6/2002 | McGucklin, Jr. et al. |
| 2002/0068899 A1 | 6/2002 | McGucklin, Jr. et al. |
| 2002/0120250 A1 | 8/2002 | Altman |
| 2002/0165489 A1 | 11/2002 | McGucklin, Jr. et al. |
| 2005/0043685 A1 | 2/2005 | Schinkel-Fleitmann |
| 2005/0187578 A1 | 8/2005 | Rosenberg et al. |
| 2005/0256458 A1 | 11/2005 | Howard et al. |
| 2005/0273058 A1 | 12/2005 | Bierman |
| 2006/0229549 A1 | 10/2006 | Haus |
| 2007/0225651 A1 | 9/2007 | Rosenberg et al. |
| 2008/0312599 A1 | 12/2008 | Rosenberg |
| 2009/0099527 A1 | 4/2009 | Rosenberg et al. |
| 2009/0143740 A1* | 6/2009 | Bierman ............ A61M 5/1415 604/177 |
| 2009/0326473 A1* | 12/2009 | Rosenberg ............ A61M 25/02 604/180 |
| 2010/0016801 A1 | 1/2010 | Rosenberg et al. |
| 2010/0081996 A1 | 4/2010 | Fink |
| 2010/0198161 A1 | 8/2010 | Propp |
| 2010/0204656 A1* | 8/2010 | Rosenberg ............ A61M 25/02 604/174 |
| 2010/0298778 A1* | 11/2010 | Bracken ................ A61M 25/02 604/180 |
| 2012/0041377 A1 | 2/2012 | Haak |
| 2012/0078191 A1 | 3/2012 | Rosenberg |
| 2014/0171899 A1 | 6/2014 | Rosenberg |

FOREIGN PATENT DOCUMENTS

| | | |
|---|---|---|
| WO | WO 2004/026152 | 4/2004 |
| WO | WO 2005/039419 | 5/2005 |
| WO | WO 2005/102438 | 11/2005 |
| WO | WO 2006/074700 | 7/2006 |
| WO | WO 2008/051810 | 5/2008 |
| WO | WO 2011/060197 | 5/2011 |
| WO | WO 2012/162251 | 11/2012 |

OTHER PUBLICATIONS

International Preliminary Report on Patentability for PCT/US2013/074621 dated Jun. 16, 2015, 11 pages.
International Search Report and Written Opinion for PCT/US2013/074621, dated Mar. 6, 2014, 15 pages.
Johnson & Johnson web page printout, "The EndoANCHOR Comparative Summary" printed Sep. 13, 2005, 2 pages.
Johnson & Johnson web page printout, "The EndoANCHOR Features and Benefits" printed Sep. 13, 2005, 2 pages.
Johnson & Johnson web page printout, "The EndoANCHOR Firing Sequences" printed Sep. 13, 2005, 2 pages.
Web Page Printout of Statlock Device, author and date unknown, 2 pages.

* cited by examiner

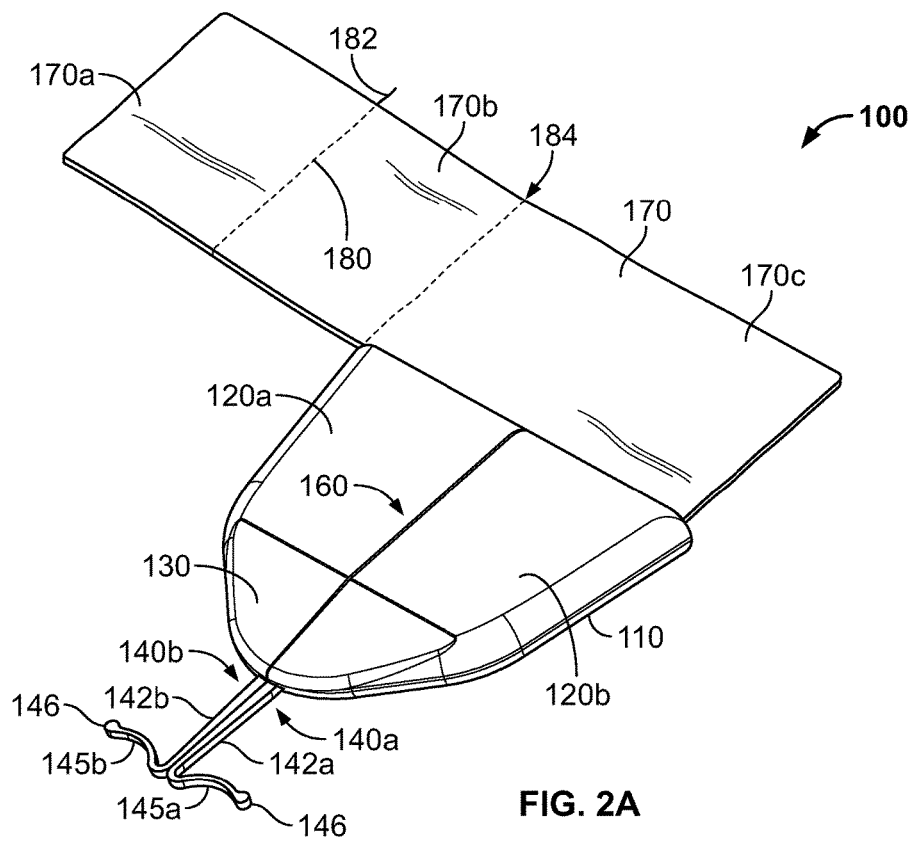
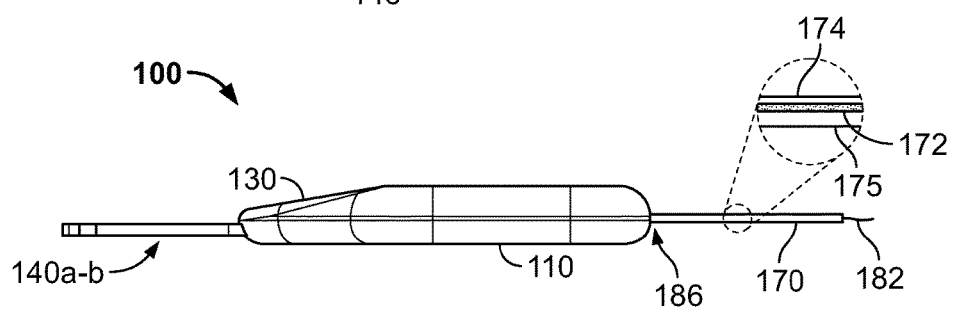
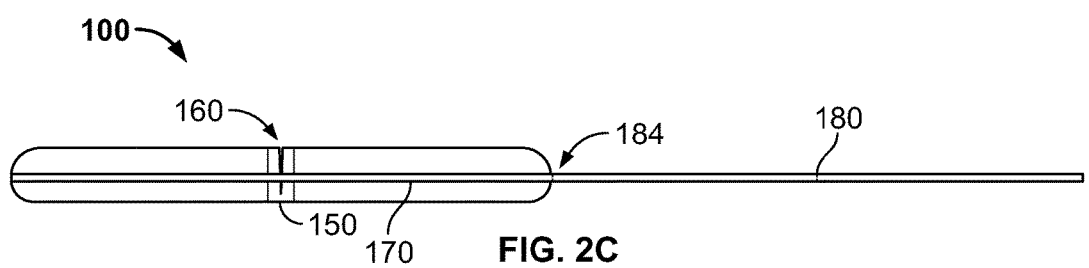
FIG. 2A
FIG. 2B
FIG. 2C

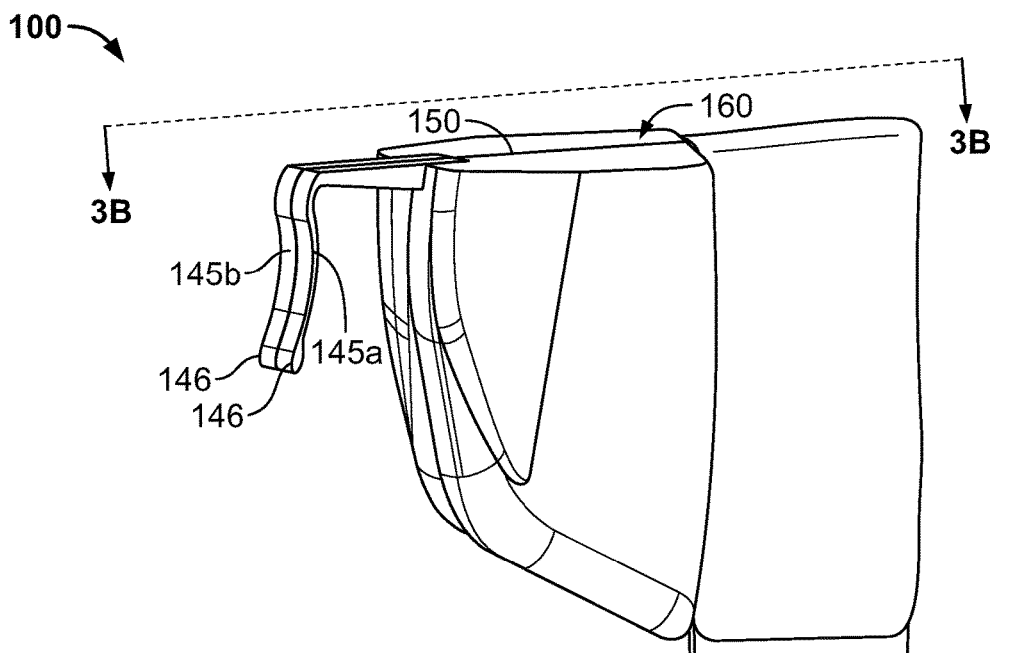
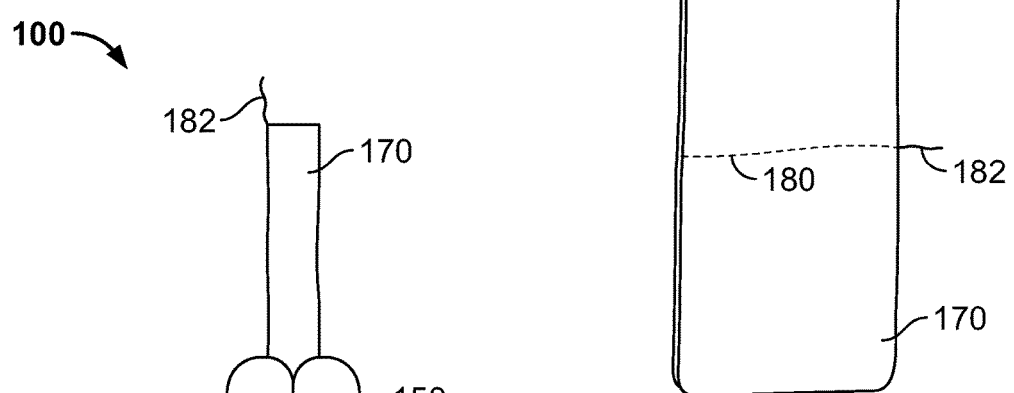
FIG. 3A
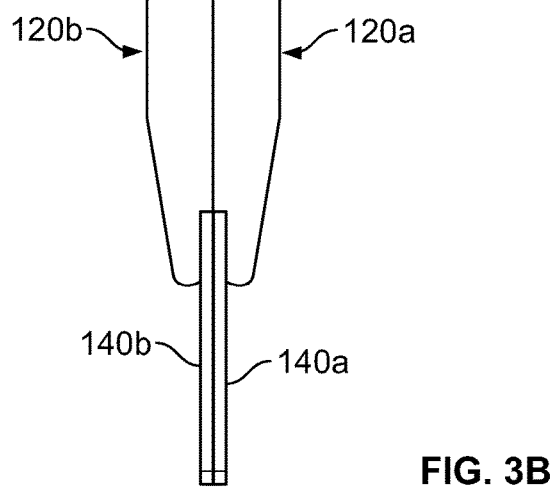
FIG. 3B

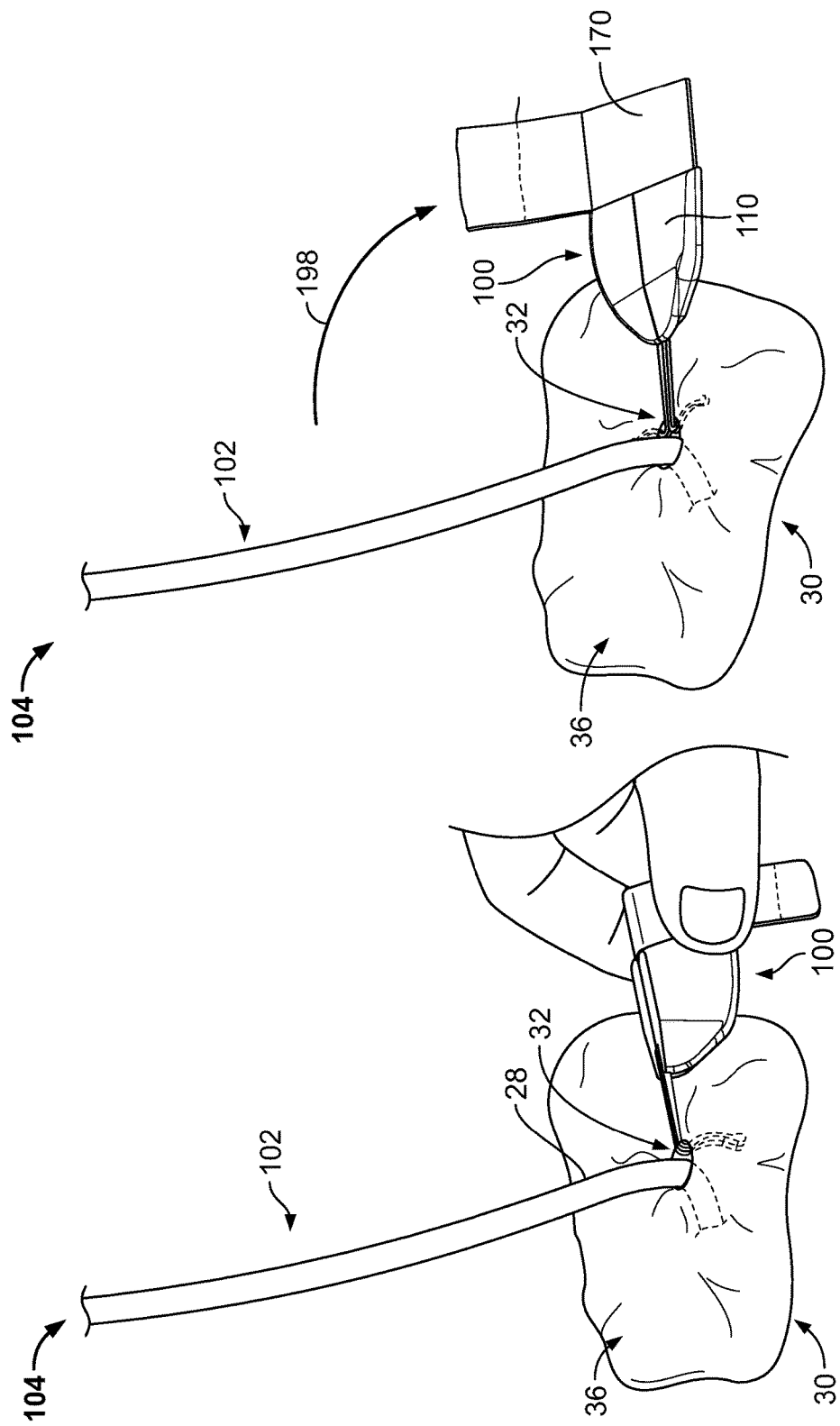

SYSTEMS AND METHODS FOR ANCHORING MEDICAL DEVICES

CLAIM OF PRIORITY

This application is a continuation of U.S. patent application Ser. No. 15/384,910 filed Dec. 20, 2016, which is a divisional application which claims priority to U.S. patent application Ser. No. 13/713,239, filed on Dec. 13, 2012, the entire contents of which are hereby incorporated by reference.

TECHNICAL FIELD

This document relates to devices, systems, and methods for securing the position of a catheter or another medical instrument, for example, at a skin opening.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Alternatively, catheters can contain electrical leads for neuro-stimulation, cardiac pacing, and the like. Following introduction into the patient, the catheter is secured to the patient. In many instances, the catheter is commonly secured to the patient using an adhesive tape on the skin or by suturing a catheter hub to the patient's skin. In other circumstances, the catheter may be secured to the patient using a subcutaneous anchor mechanism (such as an anchor sleeve equipped with anchors that are deployed using an external actuator handle or a separate delivery device). In many cases, the medical practitioner will make efforts to clean the skin area around the catheter insertion site for purposes of a patient's comfort, safety, and improved visualization of the catheter insertion site after the catheter is installed.

SUMMARY

Some embodiments of a medical device anchor system include an anchor device that provides an adhesive coupling with a medical instrument (such as a catheter or the like that is optionally equipped with suture wings) and furthermore secures the instrument in place relative to a skin penetration point. For example, the medical anchor device can be equipped with a flexible fabric portion that is configured to adhesively attach to a shaft of a hub of a catheter while the medical anchor device also provides subcutaneous anchor mechanisms deployable through the skin penetration point that is already occupied by the catheter, thereby reducing or eliminating the need for installing sutures through the suture wings and the patient's skin. Optionally, in some embodiments the anchor device can be adjusted to a folded configuration that orients the tines of the subcutaneous anchors in a generally side-by-side configuration to facilitate insertion of the anchors through the skin penetration point. Such a configuration may allow the anchor device to be installed after medical instrument is already in place without the need for a second penetration point for the anchor device. In particular embodiments, the anchor device may be configured to simplify the use of the anchor device, make the anchor device more adaptable to use with medical instruments of different sizes, and to facilitate the maintenance and cleaning of the skin tissue at and around the skin penetration point.

In particular embodiments, an anchor device for securing the position of a medical instrument may include a retainer body. The retainer body can include a first body portion that is hingedly coupled to a second body portion about a longitudinal folding region. Also, the anchor device may include one or more flexible adhesive strips mounted to the retainer body. The one or more flexible adhesive strips can be configured to adhesively attach with one or more corresponding exterior surfaces of a medical instrument. The anchor device may further include first and second anchors that extend distally from a distal end of the retainer body. Each anchor may include a flexible tine that is deployable in a subcutaneous region to secure the retainer body relative to a penetration point. The first anchor may be coupled to the first body portion, and the second anchor may be coupled to the second body portion. The first body portion of the retainer body can be hingedly movable relative to the second body portion about the longitudinal folding region so that the first and second anchors are adjustable from a first configuration in which the flexible tines extend outwardly away from one another to a second configuration in which the flexible tines extend generally in the same direction.

Some embodiments of an anchor device may include a retainer body and first and second flexible adhesive strips. The retainer body may include a first body portion that is pivotably coupled to a second body portion about a longitudinal fold axis. The first and second flexible adhesive strips may be configured to mate with an external structure of a medical instrument to adhesively couple the medical instrument to the retainer body. The first flexible adhesive strip may be mounted to the first body portion of the retainer body, and the second flexible adhesive strip may be mounted to the second body portion of the retainer body. The anchor device can also include first and second anchors that extend distally from a distal end of the retainer body. Each anchor may include a flexible tine that is deployable in a subcutaneous region to secure the retainer body relative to a penetration point. The first anchor may be coupled to the first body portion, and the second anchor may be coupled to the second body portion. The first body portion of the retainer body may be pivotable relative to the second body portion about the longitudinal fold axis so that the first and second anchors are adjustable from a first configuration in which the flexible tines extend outwardly away from one another to a second configuration in which the flexible tines extend generally in the same direction.

Other embodiments described herein include a system for securing the position of a medical instrument. The system may include a medical instrument comprising a distal portion configured to extend through a skin penetration point and into a body, and an external portion configured to reside outside the body when the distal portion extends through the skin penetration point. The system may also include an anchor device. The anchor device may comprise a retainer body including a first body portion that is pivotably coupled to a second body portion. The anchor device may also comprise one or more flexible adhesive strips mounted to the retainer body. The one or more flexible adhesive strips may be configured to adhesively attach with one or more surfaces of the external portion of the medical instrument. The anchor device may further comprise first and second anchors that extend distally from a distal end of the retainer body. Each anchor may include a flexible tine that is deployable through the skin penetration point occupied by the medical instrument and into a subcutaneous region to secure the retainer body relative to the skin penetration point. The first anchor may be coupled to the first body portion, and the second anchor may be coupled to the second body portion. The first body portion of the retainer body may be pivotable relative to the second body portion so that the first and second anchors are adjustable from one another to a removal configuration in which the flexible tines extend generally in the same direction.

Some embodiments described herein include a method of using a medical anchor system. The method may include advancing an anchor device toward a skin penetration point while the anchor device is in a folded condition so that a plurality of subcutaneous tines of the anchor device are generally adjacent to each other and oriented to extend in substantially the same direction. The method may also include inserting the subcutaneous tines through the skin penetration point and into a subcutaneous region adjacent to an underside of a skin layer while the anchor device is in the folded condition. Each of the subcutaneous tines may have a shape which terminates at a tip of a free end during insertion through the skin penetration point. The method may further include adjusting the anchor device to a non-folded condition after the subcutaneous tines are inserted into the subcutaneous layer so that the subcutaneous tines are in an anchored position in which the free ends of the subcutaneous tines extend generally away from one another. Also, the method may include adhesively securing a medical instrument to the anchor device after the subcutaneous tines are adjusted to the anchored position in the subcutaneous region. The operation of adhesively securing may include coupling one or more flexible adhesive members of the anchor device with one or more exterior surfaces of the medical instrument.

These and other embodiments may provide one or more of the following advantages. First, some embodiments of an anchor system can retain a medical instrument in a desired position relative to a skin penetration point without necessarily requiring sutures or skin adhesives. Second, particular embodiments of the anchor device may be readily adaptable to use with catheters or other medical instruments of different sizes, while also securing the catheter or medical instrument to a skin penetration point in a manner that facilitates improved inspection and cleaning of the skin tissue at and around the skin penetration point. For example, some of these particular embodiments of the anchor device can provide a capless design in which an adhesive fabric of the anchor device adhesively couples the anchor device to an external portion of the catheter or medical instrument without the need for an attachable cap device, thereby simplifying the process for a practitioner to couple the anchor device to the catheter or medical instrument. As another example, some of these particular embodiments include a tear strip in the adhesive fabric to permit a practitioner to decouple the catheter or medical device from the anchor device. Third, in some embodiments, the anchor device may be adjusted between a folded configuration and a non-folded configuration so that the subcutaneous anchors are arranged side-by-side and extend in generally the same direction during both installation through and removal from the skin penetration point. Fourth, in some embodiments, the anchor device can be installed in accordance with a technique that reduces or eliminates the need to shift the subcutaneous tines to or from a flexed or stressed configuration. Thus, in these embodiments, the subcutaneous anchors may be readily installed and removed from the skin penetration point without the need for a separate external actuator or delivery device. Fifth, in some embodiments, the configuration of the anchor device can simplify the process of installing a medical instrument onto the anchor device and removing the medical instrument from the anchor device. Sixth, in some embodiments, the anchor device can be configured to be usable with a variety of styles and sizes of medical instruments. Seventh, in some embodiments, the anchor device can enable a hub of a catheter or other medical instrument to be positioned in close proximity to the skin penetration point.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2C are perspective, side, and rear views, respectively, of the anchor device of FIG. 1.

FIGS. 3A-3B are perspective and top views, respectively, of the anchor device of FIG. 1 in a folded condition, in accordance with some embodiments.

FIGS. 4-7A are perspective views of an anchor system, including the anchor device of FIG. 1, for use in securing the position of a medical instrument.

Like reference symbols in the various drawings indicate like elements.

DETAILED DESCRIPTION OF ILLUSTRATIVE EMBODIMENTS

Figure 1:
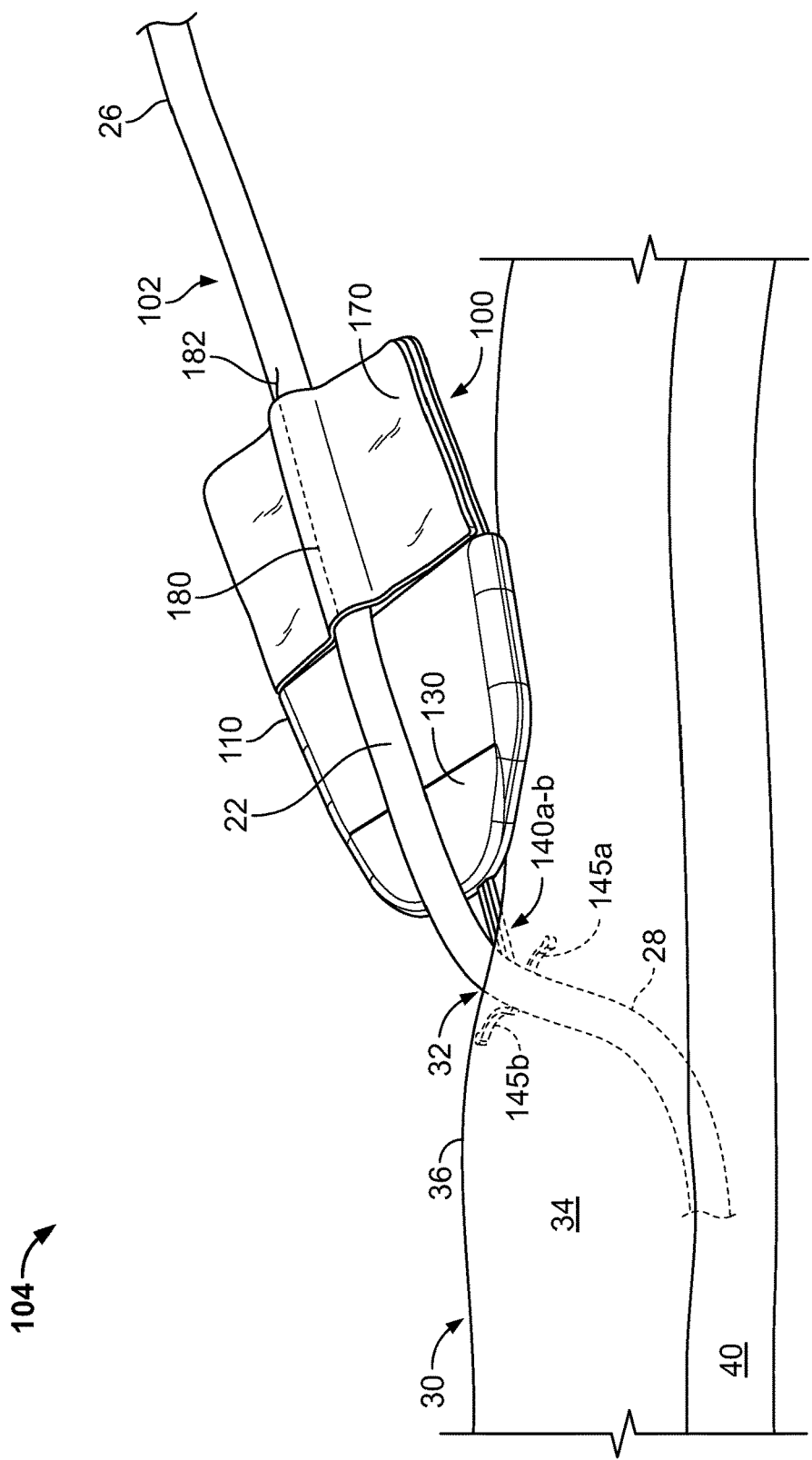
FIG. 1 is a perspective view of an anchor device with a portion of the device located in a subcutaneous region, in accordance with some embodiments.

Referring to FIG. 1, some embodiments of a medical device anchor system 104 include an anchor device 100 that adhesively attaches to a medical instrument 102 and furthermore secures the medical instrument 102 in an operative position relative to a portion of skin 30. The medical instrument 102 can be adhesively coupled to the anchor device 100 after the medical instrument 102 using, for example, a flexible fabric portion 170 having an adhesive layer thereon. The anchor device 100, in turn, can be coupled to the portion of skin 30 using one or more subcutaneous members 145*a-b*. In this manner, the anchor device 100 can act as an intermediary member to cause the retention of the medical instrument 102 in a desired position with respect to the skin 30. The example embodiment of FIG. 1 can include the medial instrument 102 (e.g., a central venous catheter 102) inserted through a percutaneous opening formed in the skin (e.g., penetration point 32), proceeding to the underside of the skin 30, and into a vein 40 to provide vascular access for delivering medications, withdrawing fluids, or providing minimally invasive access into a patient.

In this example, the anchor device 100 can generally include a retainer body 110, adhesive fabric 170, and one or more anchors 140a-b. The adhesive fabric 170 extends proximally from a proximal end of the retainer body 110. The one or more anchors 140a-b extend distally from a distal end of the retainer body 110. As described further below, the anchor device 100 can be configured to couple with the medical instrument 102. The one or more anchors 140a-b can be configured for deployment through a skin penetration point 32 and into a subcutaneous layer 34, so as to releasably retain the anchor device 100 with respect to the skin 30. For example, the anchor device 100 can include the one or more anchors 140a and 140b that extend distally from the retainer body 110 so as to penetrate through the same skin penetration point while the retainer body 110 (and the adhesive fabric 170 mounted thereto) remain external to the skin penetration point 32. In some embodiments, the skin penetration point 32 may be defined by a small incision, a puncture, or the like through the dermal layers 36.

The anchors 140a-b can include subcutaneous tines 145a-b that, after insertion, reside in the subcutaneous region 34 (e.g., a region immediately under the skin 30 that may comprise a fatty tissue layer) so as to secure the position of the anchor device—and the medical instrument 102 retained therein—relative to the penetration point 32. When the tines 145a-b are deployed in the subcutaneous region 34, the anchor device 100 can be secured to the patient without the retainer body 110 penetrating through the dermal layers 36 of the patient, and without necessarily requiring sutures or adhesive tapes bonded to the skin 30.

As described in more detail below in connection with FIGS. 4-8, the anchor device 100 can be installed into a skin penetration point 32 in accordance with a technique that reduces or eliminates the need to shift the subcutaneous tines 145a-b of the anchors 140a-b to or from a flexed or stressed configuration. As such, the anchor tines 145a-b need not undergo substantial flexing during installation or removal. In these circumstances, the subcutaneous anchors may be both installed and removed from the skin penetration point 32 advantageously without the need for an external actuator handle or delivery device to deploy the subcutaneous tines 145a-b. It should be understood that, in alternative embodiments, the anchor tines 145a-b may be flexed to a different shape during installation or removal.

Still referring to FIG. 1, after installation of the subcutaneous anchor tines 145a-b into the subcutaneous layer 34, the retainer body 110 and the adhesive fabric 170 can receive the medical instrument 102. In this embodiment, the adhesive fabric 170 receives the medical instrument 102 after a release liner 174 is removed from the adhesive fabric 170 to expose an adhesive layer 172 (FIGS. 2A-C). The release liner 174 may be removed before installation of the subcutaneous tines 145a-b through the skin opening 32 or after installation of the subcutaneous tines 145a-b through the skin opening 32. The medical instrument 102 may be placed in contact with the exposed adhesive fabric 170, and a user may fold the adhesive fabric 170 over the medical instrument 102 to secure the medical instrument 102 to the anchor device 100.

Accordingly, in some embodiments, the anchor device 100 can provide a capless design in which the anchor device 100 adhesively couples with an external portion of the medical instrument 102 without the need for attaching a cap or other similar component onto the retainer body 110, thereby simplifying the process of inspecting and cleaning the anchor device 100 and the skin surface near the skin penetration point 32 after installation. It should be understood that, in alternative embodiments, the retainer body 110 can be configured so as to mate with a cap component so as to supplement the holding force upon the medical instrument beyond the holding force provided from the adhesive fabric 170.

In the depicted example, the medical instrument 102 is embodied as a catheter. Hence, hereinafter the medical instrument 102 may alternatively be referred to as catheter 102, without limiting the medical instrument 102 to such an embodiment. In this embodiment, the example catheter 102 generally includes a proximal portion 26, a central portion 22, and a distal portion 28. The central portion 22 can interconnect the proximal portion 26 with the distal portion 28. In some embodiments, the proximal portion 26 of the catheter 102 may have multiple lumens (not shown) that are suited to deliver multiple types of solutions to the patient. In some embodiments, the catheter 102 includes a hub (e.g., hub 42 as described with respect to FIGS. 9-16) that can receive the multiple lumens on the proximal end of the hub, and merge the multiple lumens so as to connect with a single shaft of the distal portion 28.

Referring now to FIGS. 2A-2B, some embodiments of the anchor device 100 include the retainer body 110 and the anchors 140a-b, which are connected to and extend distally from the distal end of the retainer body 110. For example, the anchors 140a and 140b can be connected to the retainer body 110 using an over-molding process to secure the anchors 140a-b relative to the retainer body 110. It should also be understood that there exist many manufacturing processes that can secure the anchors 140a and 140b to the retainer body 110. In some embodiments, the retainer body 110 and the anchors 140a and 140b can be manufactured as a single, unitary piece.

In particular embodiments, the anchor device 100 can be configured to be folded longitudinally about a longitudinal fold axis 160 (e.g., a longitudinally extending region configured for enabling the retainer body 110 to repeatedly adjust from a first position to a second, folded position as shown, for example, in FIGS. 3A-3B). Consequently, the retainer body 110 can be described as having a first retainer body portion 120a and a second retainer body portion 120b. In some embodiments, the first and second retainer body portions 120a-b can be substantially mirror images of each other. In alternative embodiments, the first and second portions of the anchor device 100 can be asymmetrical.

Preferably, at least a portion of each anchor 140a-b comprises a flexible material. In some embodiments, the anchors 140a-b may comprise a material that exhibits superelasticity. In some embodiments, at least a portion of the anchors 140a-b (including the tines 145a-b) may be formed from a length of nitinol wire or from a sheet of nitinol material. Alternatively, the anchors 140a-b may comprise a metal material such as stainless steel (e.g., 304 stainless, 316 stainless, custom 465 stainless, and the like), spring steel, titanium, MP35N, and other cobalt alloys, or the like. In another alternative, the anchors 140a-b may be formed from a resilient polymer material. In some embodiments, the anchors 140a-b can be formed from a material or materials that allow the tines 145a-b to be flexed and resiliently return to an unstressed position.

In the embodiment depicted in FIGS. 2A-C, each of the anchors 140a-b may be designed such that the tines 145a-b have an unstressed position wherein the tines 145a-b have a convex curvature. The convex curvature shape of the tines 145a-b may permit the tines 145a-b to abut against the underside of the dermal layers 36 in a manner that reduces the likelihood of the tine tips 146 puncturing the underside of the dermal layers 36. Preferably, the tine tips 146 are rounded bulbs or otherwise non-sharp so as to further protect the underside of the dermal layers 36. In alternative embodiments, the tines 145a-b may have a generally straight shape that extends substantially perpendicular to the longitudinal shaft portions of the anchors 140a-b to the rounds tips 146.

The retainer body 110 can comprise one or more biocompatible polymer materials (e.g., PVC, polypropylene, polystyrene, or the like). In some embodiments, the retainer body 110 can comprise a combination of such materials, for example, when the flexible web portion comprises an elastically flexible silicone material while the first and second retainer body portions 120a-b comprise a less flexible polymer material such as polypropylene, PVC, polystyrene, or the like. In some embodiments, the retainer body 110 can be formed using a molding process in which the retainer body 110 is over-molded around a portion of the anchors 140a-b, especially in those embodiments in which the anchors 140a-b comprise a metallic material. For example, the left retainer body portion 120a can be over-molded around a portion of anchor 140a and, during the same or a different molding process, the right body portion 120b can be over-molded around a portion of anchor 140b. Consequently, as described further below, when the retainer body 110 is folded, the respective anchors 140a-b (being connected to the retainer body portions 120a-b respectively) likewise move in conjunction with their respective retainer body portion 120a-b.

Still referring to FIGS. 2A-C, the adhesive fabric 170 of the anchor device is optionally mounted to the retainer body 110 so that the adhesive fabric 170 extends proximally away from a proximal end of the retainer body 110 (e.g., extends away from the anchors 140a-b). The adhesive fabric 170 may include a flexible substrate 175 on which an adhesive layer 172 has been formed (see FIG. 2B). For example, the flexible substrate 175 may comprise a mesh material or flexible woven material. The anchor device 100 may be manufactured with a releasable liner 174 covering the adhesive layer 172 to preserve the adhesive characteristics and to limit exposure of the adhesive layer 172 to environmental contaminants prior to user removal of the releasable liner 174. In practice, a user may readily remove the releasable liner 174 from the adhesive fabric 170 after installation of the subcutaneous anchor tines 145a-b into the subcutaneous layer 34. The user may thereafter place the catheter 102 in contact with the adhesive layer 172, and fold a portion of the adhesive fabric 170 over top of the catheter 102 and onto another portion of the adhesive fabric. In this way, the catheter 102 may be sandwiched between two portions of the adhesive fabric 170, securing the catheter 102 to the anchor device 100. Thus, although the adhesive layer 172 is employed to secure the catheter 102 to the anchor device 100, the catheter 102 is anchored to the skin 30 using the subcutaneous tine 145a-b (without the need to apply an adhesive directly to the skin 30).

In some embodiments, the adhesive fabric 170 may include a tear strip 180 that extends in a generally longitudinal direction (e.g., generally parallel to the longitudinal fold axis 160 of the retainer body 110). The adhesive fabric may be adapted such that pulling the tear strip 180 results in the adhesive fabric 170 separating along an installation of the tear strip 180 in the adhesive fabric 170. Said another way, the tear strip 180 may be adapted to separate the adhesive fabric 170 into multiple portions as a result of a user pulling the tear strip 180 away from the adhesive fabric 170, for example, in a direction that is generally traverse to a plane of the adhesive fabric 170. The tear strip 180 may embody a continuous polymer thread that is located within one or more layers of the flexible substrate 175. Optionally, the flexible substrate 175 may be perforated along the location of the tear strip 180 to facilitate separation of the adhesive fabric 170 as a result of the user pulling the tear strip 180 away from the adhesive fabric 170. The tear strip 180 may be manufactured with sufficient tensile strength to remain intact as the user pulls the tear strip 180 away from the adhesive fabric 170, and as the adhesive fabric 170 is ripped into two portions through force applied to the adhesive fabric 170 by the tear strip 180.

In some embodiments, the tear strip 180 may include a protruding portion 182 that is adapted to be grasped by the user with an instrument or between the user's fingers. The protruding portion 182 may be a most-proximal portion of the anchor device 100. The tear strip 180 may be positioned in the adhesive fabric 170 such that the tear strip 180 is located generally longitudinally along the catheter 102 when the adhesive fabric 170 is folded over the catheter 102. In this manner, after the catheter 102 has been secured to the anchor device 100, the practitioner is able to remove the catheter 102 from the anchor device 100 by pulling the tear strip 180 away from the adhesive fabric 170, separating the adhesive fabric 170 along a length of the catheter 102 and permitting removal of the catheter 102 through the separation in the adhesive fabric 170 while the adhesive fabric remains adhesively bonded to itself. The user may not grasp, for example, a corner of the adhesive fabric 170 and peel the corner of the adhesive fabric 170 off another portion of the adhesive fabric 170. Thus, after adhesive coupling of the catheter 102 to the anchor device 100, the catheter 102 may be removed in a straightforward manner from contact with the anchor device 100 and subcutaneous region 34 before the tines 145a-b are removed from the subcutaneous region 34. Said another way, the anchor device 100 may be removed from the subcutaneous region 34 after catheter 102 has been removed from contact with the anchor device 100 and the subcutaneous region 34. The adhesive fabric 170 may remain folded over and adhesively bonded to itself (although separated into multiple portions) during removal of the anchor device 100 from the subcutaneous region 34.

The flexible substrate 175 of the adhesive fabric 170 can be manufactured from a flexible material such as a textile mesh, a polymer mesh, a polymer sheet, a flat web of polymer foam material, or a metallic foil. The adhesive layer 172 may comprise an adhesive, for example, a suitable medical adhesive. In some examples, a medical adhesive that is robust to cleaning agents and that provides a permanent hold may be employed as the adhesive layer 172. The releasable liner 174 may be formed of a polymer sheet or a wax paper, for example.

Still referring to FIGS. 2A-C, the adhesive fabric 170 can be configured to provide an effective coupling interface with the catheter 102 or other medical instrument, while providing features that simplify the overall use of the medical device anchor system 10. For example, in this embodiment, the adhesive fabric 170 may provide the user with a simplified coupling technique for mating the anchor device 100 to the catheter 102, and may furthermore do so without the need for an attachable cap device. In the depicted example, the adhesive fabric 170 in general is mounted to the retainer body 110, for example, so that the adhesive fabric may be folded along a fold axis 184 of the adhesive fabric 170 (e.g., a longitudinally extending region configured for the adhesive fabric 170 to fold upon itself). The fold axis 184 of the adhesive fabric 170 may be offset from but parallel to the longitudinal fold axis 160. The tear strip 180 may be located such that the tear strip 180 is substantially with the longitudinal fold axis 160 when the adhesive fabric 170 has been folded along the fold axis 184 (refer to FIG. 1). The tear strip 180 and the fold axis 184 of the adhesive fabric 170 can define borders between different regions of the adhesive fabric 170. Consequently, the adhesive fabric 170 can be described as having a first adhesive fabric portion 170a, a second adhesive fabric portion 170b, and third adhesive fabric portion 170c.

The adhesive and flexible characteristics of the adhesive fabric 170 enables a user to fold the first adhesive fabric portion 170a and the second adhesive portion 170b into adhesive contact with both the catheter 102 and the third adhesive fabric portion 170c. In this manner, the first adhesive fabric portion 170a and the second adhesive fabric portion 170b each adhere to both the catheter 102 and the third adhesive fabric portion 170c. Furthermore, the third adhesive fabric portion 170c may adhere with the catheter 102. Thus, when securing the medical device 102 to the retainer body 110, the user can place the catheter 102 in contact with the adhesive fabric 170, for example, along the longitudinal fold axis 160, and can thereafter fold the adhesive fabric 170 along the fold axis 184 (which may include a visual indicia of the fold axis 184, such as a solid or dotted line imprinted on the adhesive fabric 170). During the folding, the user may align the tear strip 180 with the catheter 102 and press the second adhesive fabric portion 170b onto the catheter 102 and the third adhesive fabric portion 170c, and can press the first adhesive fabric portion 170a onto the catheter 102 and the third adhesive fabric portion 170c. The contact of the catheter 102 with the first adhesive fabric portion 170a, the second adhesive fabric portion 170b, and the third adhesive fabric portion 170c may result in a snug coupling of the catheter 102 to the anchor device 100.

In the embodiment shown in FIG. 2B, the adhesive fabric 170 is molded into a proximal portion of the retainer body 110 at junction 186, for example, with an insert molding operation. In another example, junction 186 may be a slot that is formed during a molding process, and the adhesive fabric 170 is bonded into the slot with a permanent adhesive during a manufacturing assembly process. In yet another example, the adhesive fabric 170 may be mechanically fastened into junction 186. In an alternative example, the adhesive fabric 170 may include a tongue portion that is mechanically fastened or permanently adhered to an underside of the retainer body 110 so that the adhesive fabric 170 extends proximally away from the proximal end of the retainer body 110.

As will be described further below, the adhesive coupling of the catheter 102 to the anchor device 100 generally restrains movement of the medical instrument 102 away from the skin penetration point 32. Further, the limited angular freedom of movement provided by the anchors 140a-b permits the shaft of the catheter 102 to closely align with the skin penetration point 32 and reduce the stresses applied by the catheter 102 at the skin penetration point 32.

As shown in FIGS. 2A-B, some embodiments of the anchor device 100 also include a sloped nose region 130 along the retainer body 110. The sloped nose region 130 can be a generally planar surface near the distal end of the retainer body 110 that is oriented at a different angle than the generally planar surfaces of the first and second retainer body portions 120a-b. The sloped nose region 130 can decline from the generally planar surfaces of the first and second retainer body portions 120a-b such that the nose region 130 slopes downward in a distal direction towards longitudinal shafts 142a-b of the anchors 140a-b (e.g., and thus downward to the skin penetration point 32 when the anchor tines 145a-b are deployed). The sloped nose region 130 can facilitate an orientation of the distal portion 28 of the medical instrument 102 that is directed toward the skin penetration point 32. In this manner, the stresses that can potentially be exerted on the skin 30 proximal to the skin penetration point 32 by the distal portion 28 of the medical instrument 102 can be reduced.

As shown in FIG. 2C, a flexible web portion 150 of the retainer body 110 can be positioned, for example, generally centrally between the first and second retainer body portions 120a-b. As previously described, the flexible web portion 150 can extend longitudinally from a distal face of the retainer body 110 to a proximal face of the retainer body 110, and can be used to define the fold axis 160 about which the first and second retainer body portions 120a-b are pivotable from the non-folded condition (FIG. 2A) to the folded condition (FIG. 3A). The flexible web portion 150 can comprise an elastically flexible biocompatible polymer material (e.g., silicon, PVC, polypropylene, polystyrene, or the like). In some embodiments, the flexible web portion 150 can be made of the same material as the other portions of the retainer body 110. In other embodiments, the flexible web portion 150 can be made of a different material than the other portions of the retainer body 110. In such a case, the anchor device 100 can be made, for example, using a two-step insert molding operation. The flexible web portion 150 can be biased to resiliently maintain the non-folded shape of the anchor device 100 as depicted in FIGS. 2A-2C. When the anchor device 100 is folded along the fold axis 160 due to a user's grasp (refer, for example, to FIG. 4), the flexible web portion 150 can undergo elastic deformation such that flexible web potion 150 biases the anchor device 100 to return the non-folded condition (FIGS. 2A and 5) upon release from the user. In addition or alternatively, the fabric 170 may also stretch along the longitudinal axis 160 and bias the anchor device 100 to return to the non-folded condition. In some embodiments, the fabric 170 may be two separate pieces of fabric that do not span the longitudinal fold axis 160, such that the two separate pieces of fabric are not stretched at a location of the longitudinal fold axis 160 when the anchor device is in the folded condition.

Referring now to FIGS. 3A-3B, in this example embodiment, the anchor device 100 may include features that allow the individual anchors 140a-b to be moved relative to each other so as to facilitate both insertion and removal of the anchor device 100 through the skin penetration point 32. For example, the anchor device 100 may have a foldable configuration in which a first portion of the retainer body 110 is pivotably coupled via a flexible hinge portion to a second portion of the retainer body 110.

More specifically, in this embodiment, the first retainer body portion 120a and the second retainer body portion 120b can be flexibly pivoted with respect to each other along a fold axis 160 extending longitudinally through the retainer body 110. To initiate the folding process of the anchor device 100, the user can apply a bending moment about the fold axis 160 to the first and second retainer body portions 120a-b. Such a bending moment can cause an elastic deformation of the flexible web portion 150 so as to fold the anchor device along the fold axis 160 (refer to FIG. 3A). Because the adhesive fabric portion 170 comprises the flexible substrate 175 and liner 174, the adhesive fabric portion 170 is sufficiently compliant to temporarily fold with the retainer body 110 during this operation. The first retainer body portion 120a can be fixedly coupled to the anchor 140a, and the second retainer body portion 120b can be fixedly coupled to the anchor 140b. Thus, as shown in FIGS. 3A, when the first and second retainer body portions 120a-b are pivoted about the fold axis 160, the two anchors 140a-b likewise pivot relative to one another. This process of pivoting can cause the anchor device to transition from a non-folded condition (shown in FIGS. 2A-2C and in FIG. 1) in which the tines 145a-b extend generally away from one another to a folded condition (shown in FIGS. 3A-3B), in which the tines 145a-b are generally adjacent to each other and oriented to extend in substantially the same direction. Similarly, when the bending moment from the user is released, the anchor device can be biased to return the anchor device 100 from the folded condition to the non-folded condition. In the depicted embodiment, the tines 145a-b can be rotated about 75-degrees to about 105-degrees, and preferably about 90-degrees, during the transition between the non-folded condition and the folded condition. As described in more detail below, the anchor device 100 can be arranged in the folded condition during both insertion and removal of the subcutaneous tines 145a-b so as to reduce the likelihood of the tines 145a-b causing damage to the skin 30.

Referring now to FIGS. 4-5, as previously described, the medical instrument 102 can optionally include a catheter to be inserted through the penetration point 32 of the skin 30 as part of a medical procedure. For example, in the embodiment depicted in FIG. 1, a central venous catheter 102 can be inserted into a percutaneous opening surgically formed in the skin (e.g., penetration point 32), to the underside of the skin 30, and into a vein 40 to provide vascular access for delivering medications or minimally invasive devices into a patient.

After placement of the catheter 102 through the penetration point 32 of the skin 30, the user can grasp the anchor device 100 in the folded condition and approach the penetration point 32 such that the free ends of the tines 145a-b are contemporaneously inserted through the penetration point 32 while the tines 145a-b are in a generally side-by-side condition (as depicted in FIG. 4). In particular embodiments, the subcutaneous tines 145a-b are inserted through the skin penetration point 32 while the user conveniently grasps the retainer body 110 of the anchor device 100 and applies an insertion force until the convexly curved body portions of the subcutaneous tines 145a-b are positioned below the surface of the skin 30 (while the remainder of the anchor device 100 resides external to the skin 30).

As the anchor device 100 is inserted through the penetration point 32, the tines 145a-b are maintained in a generally non-stressed configuration (e.g., a first shape or a steady-state shape) while passing through the penetration point 32 in a manner that reduces the likelihood of trauma to the surrounding skin tissue 30. As the tines 145a-b are collectively advanced through the penetration point 32, the free ends of the tines 145a-b are moved beneath the dermal skin layers 36 of the skin 30.

When the tines 145a-b reach the subcutaneous region 34, the retainer body 110 can adjusted to the unfolded condition so that the tines 145a-b are shifted relative to one another, resulting in the tines 145a-b extending outwardly away from one another (as depicted in FIG. 5). During that process of unfolding the retainer body 110, each tine 145a-b may retain their generally non-stressed configuration (e.g., the first shape or the steady-state shape). Thus, the anchor device 100 can be installed in accordance with a technique that reduces or eliminates the need to shift the subcutaneous tines 145a-b to or from a flexed or stressed configuration during the passage through the skin penetration point 32. Also, the adhesive fabric portion 170 of the anchor device 100 is sufficiently compliant to temporarily fold and unfolded with the retainer body 110 during this process.

As previously described, the anchor device 100 can secure the catheter 102 or other medical instrument relative to a skin penetration point 32. With the anchor device 100 positioned such that subcutaneous tines 145a-b are in their deployed configuration, as shown in FIG. 5, the user may remove the releasable liner 174 of the adhesive fabric 170, exposing the adhesive layer 174 of the adhesive fabric 170. (Alternatively, the user may remove the releasable liner 174 before installation of the subcutaneous tines 145a-b into the subcutaneous region 34.) After the releasable liner 174 has been removed, the previously inserted catheter 102 can be placed in contact with the adhesive layer 174 of the adhesive fabric 170. As shown in FIG. 5, the directional arrow 198 depicts an example motion of manually positioning the catheter 102 in contact with the adhesive fabric 170 to prepare for the coupling of the catheter 102 to the anchor device 100.

Figure 6A:
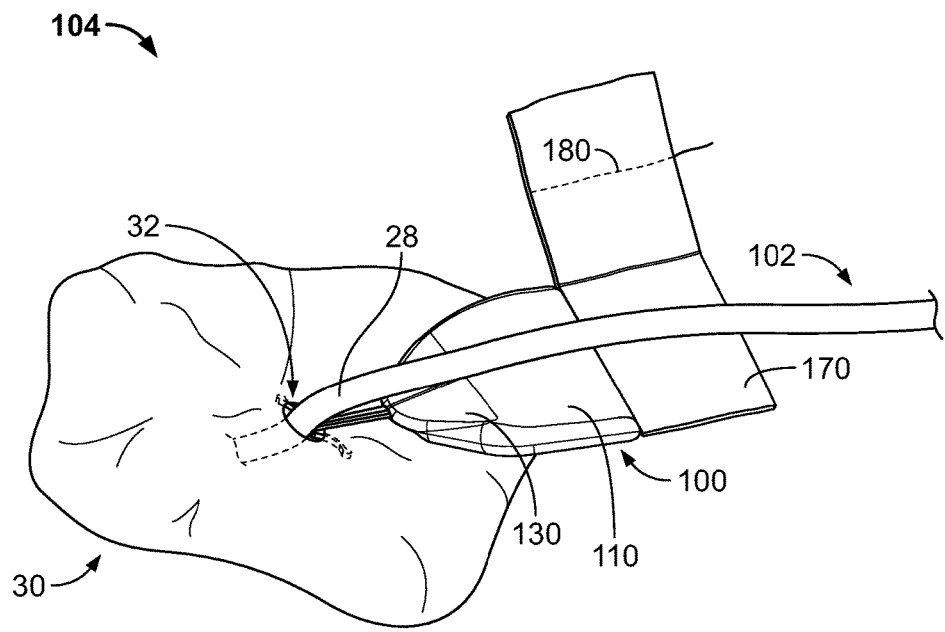
Figure 6B:
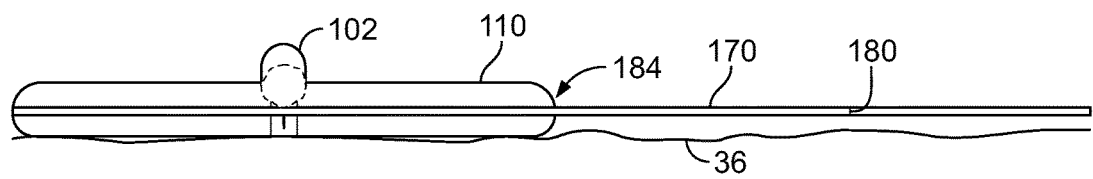

Referring now to FIGS. 6A-B, the catheter 102 can be placed in contact with the anchor device 100 so that the shaft of the catheter 102, for example, is generally aligned with the folding region 150 of the retainer body 110. In doing so, the catheter 102 is placed in contact with the adhesive layer 172 of the third portion 170c (FIG. 2A) of the adhesive fabric 170, thereby temporarily retaining the catheter 102 is a position to receive the remaining portions 170a-b of the adhesive fabric 170 over an upper side of the catheter 102. In order to adhesively couple the catheter 102 to the anchor device 102, the user may fold the adhesive fabric 170 (with the adhesive layer 172 exposed) along the fold axis 184 (FIG. 2A) and onto the catheter 102, aligning the tear strip 180 with the shaft of the catheter 102.

Figure 7A:
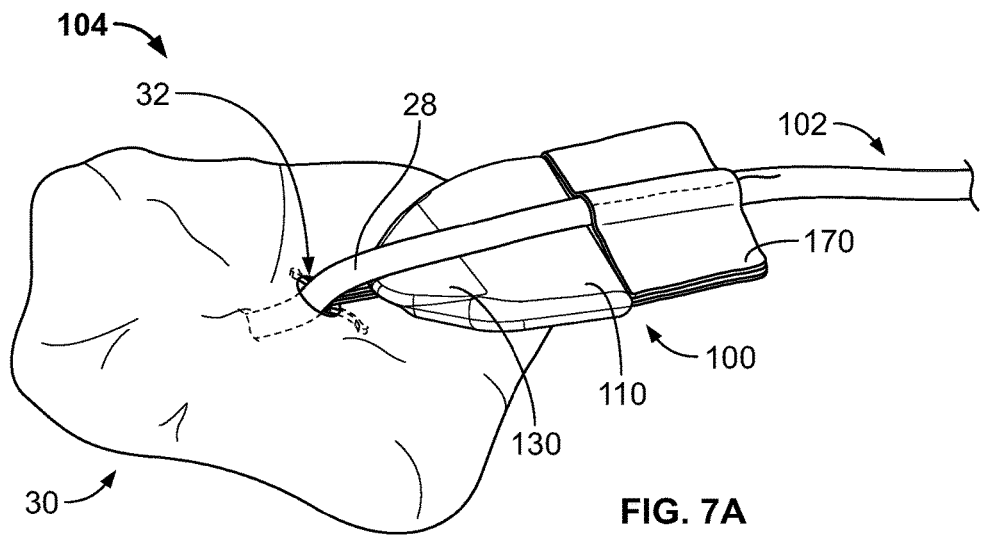
Figure 7B:
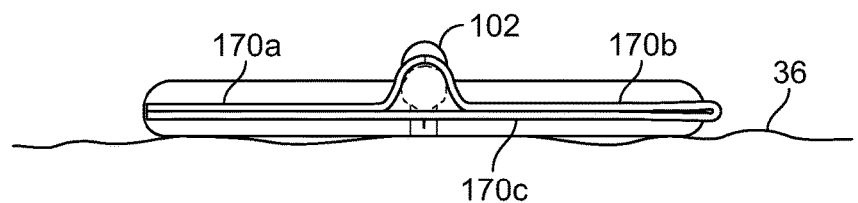
FIG. 7B is a rear view of the anchor system, including the anchor device of FIG. 1.

Referring now to FIGS. 7A-B, the anchor device of FIGS. 4-5 is adhesively coupled to the catheter 102. For example, the adhesive fabric 170 has been folded along the fold axis 184 over the catheter 102. The catheter 102 may be firmly secured between the upper and lower portions of adhesive fabric 170. In the embodiment shown in FIGS. 7A-B, the first adhesive fabric portion 170a is in adhesive contact with the third adhesive fabric portion 170c while the second adhesive fabric portion 170b is in adhesive contact with the third adhesive fabric portion 170c. The first adhesive fabric portion 170a, the second adhesive fabric portion 170b, and the third adhesive fabric portion 170c may all contact the catheter 102. In this embodiment, the adhesive coupling of the catheter 102 to the anchor device 100 secures the catheter 102 to the anchor device along at least two regions of the catheter 102 that are on opposing sides of the catheter 102. With the adhesive fabric 170 folded over itself and adhesively secured to itself and the catheter 102, the catheter 102 is fixed to the anchor device 100.

Figure 8:
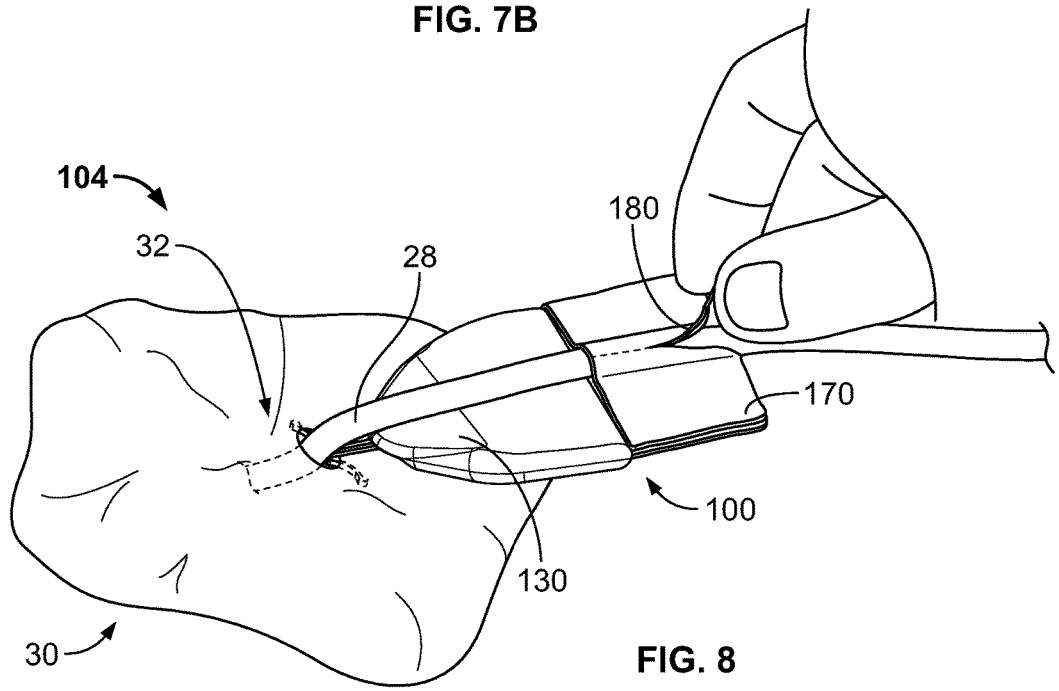
FIG. 8 is a perspective view of the anchor system, including the anchor device of FIG. 1.

FIG. 8 illustrates an example of removing of the catheter 102 (or other medical instrument) from the anchor device 100. In this example, the user can grasp the protruding portion 182 of the tear strip 180, and pull the protruding portion 182 away from the adhesive fabric 170, ripping the adhesive fabric 170 at the location of the tear strip 180 and permitting removal of the medical device 102 through the separation in the adhesive fabric 170. FIG. 8 shows the system 104 during removal of the tear strip 180 and ripping of the adhesive fabric 170, but it should be understood that the tear strip 180 may be completely removed from the adhesive fabric 170, resulting in a complete separation of the adhesive fabric 170, for example, along the previous location of the tear strip 180. It is after the complete separation of the adhesive fabric 170 that the catheter 102 may be removed from contact with the anchor device 100. In some examples, the catheter 102 is removed from contact with both the subcutaneous layer 34 and the anchor device before the subcutaneous tines 145a-b are removed from the subcutaneous layer 34.

In some embodiments, some components of the system 104 can be provided in a sterilized kit that pairs a particular type of catheter 102 or other medical instrument with a corresponding anchor device 100. The particular type of catheter 102 or other medical instrument in the kit is compatible for adhesively mating with the anchor device 100 the kit. Each kit can include one or more anchor devices 100 and the particular type of catheter 102 or other medical instrument enclosed within a flexible packaging material, which preferably includes indicators that identify the type of catheter 102 or other medical instrument that is provided along with instructions for deploying and removing the anchor device 100. The kit may include a one-to-one ratio for the quantity of anchor devices 100 to the quantity of catheters 102. In other embodiments, the kit may include multiple anchor devices 100 (e.g., having differently sized or shaped tines 145a-b) for each catheter 102 contained therein.

Alternatively, in some embodiments, the anchor device 100 can be provided in individual, sterilized packets so that a user can readily open such a packet and access the selected anchor device prior to insertion into the skin penetration point. Such individual packets can include a single anchor device enclosed within a flexible packaging material, which preferably includes indicators that identify the types of catheters or other medical instruments that are compatible for adhesively mating with the anchor device 100. As such, a user can readily select one of the packets for use after the type of catheter or medical instrument is selected for a particular patient.

FIGS. 9-16 show embodiments of a medical device anchor system 204 that is similar in some respects to the medical device anchor system 104. The medical device anchor system 204 includes an anchor device 200 that includes one or more adhesive fabric strips 270a-b with multiple tear strips 280a-b.

Figure 9:
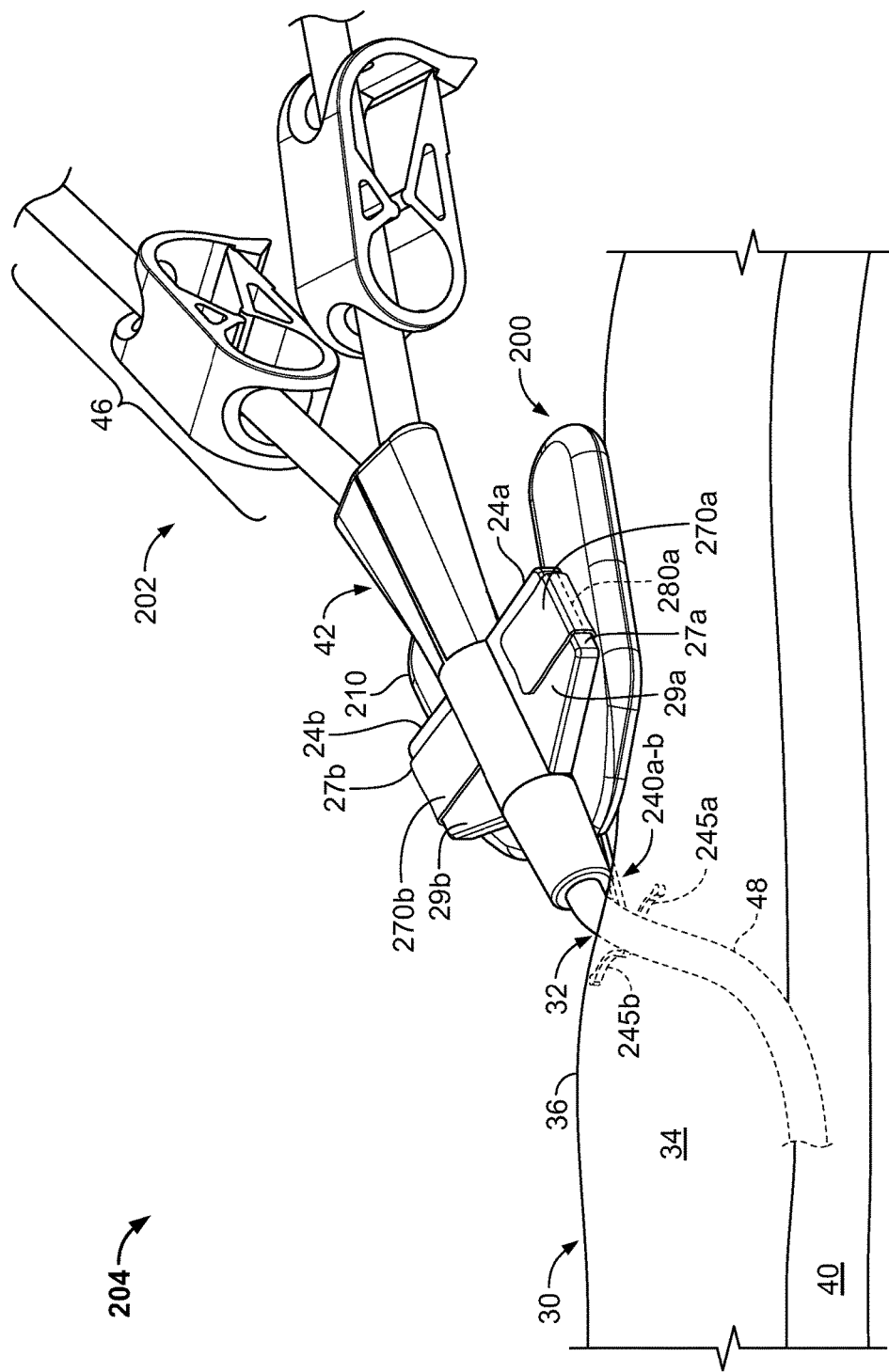
FIG. 9 is a perspective view of an anchor device with a portion of the device located in a subcutaneous region, in accordance with some embodiments.

Referring to FIG. 9, some embodiments of the medical device anchor system 204 include an anchor device 200 that adhesively retains a medical instrument 202 in an operative position relative to a portion of skin 30. The medical instrument 202 can be adhesively coupled to the anchor device 200. The anchor device 200, in turn, can be coupled to the portion of skin 30. In this manner, the anchor device 200 can act as an intermediary member to cause the retention of the medical instrument 202 in a desired position with respect to the skin 30. The example embodiment of FIG. 9, can include a medical device 202 (e.g., a central venous catheter) inserted through a percutaneous opening formed in the skin (e.g., penetration point 32), proceeding to the underside of the skin 30, and into a vein 40 to provide vascular access for delivering medications, withdrawing fluids, or providing minimally invasive access into a patient.

In this example, the anchor device 200 can generally include a retainer body 210, adhesive fabric 270a-b, and one or more anchors 240a-b. The anchors 240a-b extend distally from a distal end of the retainer body 210. As described further below, the anchor device 200 can be configured to couple with the medical instrument 202. The one or more anchors 240a-b can be configured for deployment through a skin penetration point 32 and into a subcutaneous layer 34, so as to releasably retain the anchor device 200 with respect to the skin 30. For example, the anchor device 200 can include the one or more anchors 240a and 240b that extend distally from the retainer body 210 so as to penetrate through the same skin penetration point 32 while the retainer body 210 and the adhesive fabric 270a-b remain external to the skin penetration point 32.

The anchors 240a-b can include subcutaneous tines 245a-b that, after insertion, reside in the subcutaneous region 34 so as to secure the position of the anchor device—and the medical instrument 202 retained therein—relative to the penetration point 32. When the tines 245a-b are deployed in the subcutaneous region 34, the anchor device 200 can be secured to the patient without the retainer body 210 penetrating through the dermal layers 36 of the patient, and without necessarily requiring sutures or adhesive tapes bonded to the skin 30.

As described in more detail below in connection with FIGS. 12-16, the anchor device 200 can be installed into the skin penetration point 32 in accordance with a technique that reduces or eliminates the need to shift the subcutaneous anchors tines 245a-b of the anchors 240a-b to or from a flexed or stressed configuration. As such, the anchor tines 245a-b need not undergo substantial flexing during installation or removal. In these circumstances, the subcutaneous anchors may be both installed and removed from the skin penetration point 32 advantageously without the need for an external actuator handle or delivery device to deploy the subcutaneous tines 245a-b.

Still referring to FIG. 9, after installation of the subcutaneous anchor tines 245a-b into the subcutaneous layer 34, the retainer body 210 and the adhesive fabric strips 270a-b can receive the medical instrument 202. For the adhesive fabric strips 270a-b to receive the medical instrument 202, a user may have removed releasable liners 274a-b from the adhesive fabric strips 270a-b to expose adhesive layers 272a-b. The releasable liners 274a-b may have been removed before installation of the subcutaneous tines 245a-b or after installation of the subcutaneous tines 245a-b. The medical instrument 202 may be placed in contact with the exposed adhesive fabric strips 270a-b, and a user may fold the adhesive fabric strips 270a-b over the medical instrument 202.

In this example, the medical instrument 202 is embodied as a catheter. Hence, hereinafter the medical instrument 202 may alternatively be referred to as catheter 202, without limiting the medical instrument 202 to such an embodiment. Furthermore, in some embodiments, the anchor device 200 can provide a capless design in which the anchor device 200 adhesively couples with an external portion of the catheter 202 without the need for attaching a cap onto the retainer body 210, thereby simplifying the process inspecting and cleaning the anchor device 200 and the skin surface near the skin penetration point 32 after installation.

In this embodiment, the example catheter 202 generally includes a proximal portion 46, a hub 42, and a distal portion 48. The hub 42 can interconnect the proximal portion 46 with the distal portion 48. In some embodiments, the proximal portion 46 of the catheter 202 may have multiple lumens that are suited to deliver multiple types of solutions to the patient. In some such embodiments, the hub 42 can receive the multiple lumens on the proximal end of the hub 42, and merge the multiple lumens so as to connect with a single lumen distal portion 48. For example, as shown in FIG. 9, the proximal portion 46 is depicted as having two lumens, and the distal portion 48 as having a single lumen that is adapted for percutaneous insertion through skin penetration point 32. Hence, the hub 42 can serve the purpose of merging multiple proximal supply lumens into a single distal delivery lumen suited for insertion into the patient.

The hub 42 can further be arranged to couple the catheter 202 onto the anchor device 200. In some embodiments, the hub 42 can include wings 24a-b. The wings 24a-b can have features that facilitate the coupling of the hub 42 to the anchor device 200. For example, the wings 24a-b may be shaped to adhesively couple with the one or more adhesive fabric strips 270a-b. As another example, some embodiments of the hub 42 can include apertures 47a-b in the wings 24a-b (see FIG. 13). The apertures 47a-b can be located and sized to couple with corresponding features of anchor devices that may not include the adhesive fabric strips 270a-b.

The hub 42 can be manufactured from an elastomeric or otherwise flexible material, such as silicone or another biocompatible polymer material (e.g., PVC, polypropylene, polystyrene, or the like). In some embodiments, the hub 42 can be made from a combination of materials. For example, at least wings 24a-b may comprise silicone or another flexible biocompatible material so that the wings 24a-b and the apertures 47a-b can flexibly adjust to couple with the adhesive fabric strips 270a-b or the above-described retention posts, whereas the portions of the hub 42 other than the wings 24a-b may comprise a more rigid polymer material.

The anchor device 200 can be configured to adhesively couple to the catheter 202 through use of the multiple adhesive fabric strips 270a-b. A user may wrap the adhesive fabric strips 270a-b around the wings 24a-b, respectively. The adhesive fabric strips 270a-b may include backing layers 275a-b on which adhesive layers 272a-b have been formed (see FIG. 10C). The anchor device 200 may be manufactured so that releasable liners 274a-b cover the adhesive layers 272a-b to limit exposure of the adhesive layers 272a-b to environmental contaminants and gases prior to user removal of the releasable liners 274a-b. In practice, a user may remove the releasable liners 274a-b from the adhesive fabric strips 270a-b after installation of the subcutaneous anchor tines 245a-b into the subcutaneous layer 34. The user may thereafter place the catheter 202 in contact with the retainer body 210, and fold portions of the adhesive fabric strips 270a-b over top of the wings 24a-b. In this way, the wings 24a-b of the catheter 202 may be retained by at least portions of the adhesive fabric strips 270a-b, securing the catheter 202 to the anchor device 200.

Each of the adhesive fabric strips 270a-b may include a tear strip (e.g., tear strip 280a or 280b in the depicted embodiment). As discussed with respect to the adhesive fabric 270 of FIGS. 1-8, each of the adhesive fabric strips 270a-b may be adapted such that pulling the respective tear strip 280a or 280b results in the adhesive fabric 270a or 270b separating along an installation of the tear strip 280a or 280b in the adhesive fabric 270a or 270b. The tear strips 270a-b, backing layers 275a-b, and adhesive layers 272a-b may be constructed of the same materials and function similarly to the tear strip 170, flexible substrate 175, and adhesive layer 272 that are described with reference to FIGS. 1-8. The tear strips 280a-b may include protruding portions 282a-b that are adapted to be grasped by the user with an instrument or between the user's fingers.

The tear strips 280a-b may be positioned in the adhesive fabric strips 270a-b such that the tear strips 280a-b generally run alongside surfaces 27a-b when the adhesive fabric strips 270a-b are folded over top surfaces 29a-b of the wings 24a-b. In this manner, after the catheter 202 has been secured to the anchor device 200, the user is able to remove the catheter 202 from the anchor device 200 by pulling the tear strips 280a-b away from the adhesive fabric strips 270a-b, separating the adhesive fabric strips 270a-b along the locations of the side surfaces 27a-b and permitting removal of the catheter 202, for example, without requiring the user to grasp corners of the adhesive fabric strips 270a-b and peel the adhesive fabric strips 270a-b off the wings 24a-b. Indeed, portions of the adhesive fabric strips 270a-b may remain adhesively bonded to the wings 24a-b after removal of the catheter 202. Thus, after adhesive coupling of the catheter 202 to the anchor device 200, the catheter 202 may be removed in a straightforward manner from contact with the retainer body 210 and the subcutaneous region 34 before the tines 245a-b are removed from the subcutaneous region 34. Said another way, the anchor device 200 may be removed from the subcutaneous region 34 after catheter 202 has been removed from contact with the anchor device 200 and the subcutaneous region 34 (except that the separated regions of the adhesive fabric strips 270a-b may remain in contact with the wings 24a-b after pulling of the tear strips 280a-b).

Figure 10A:
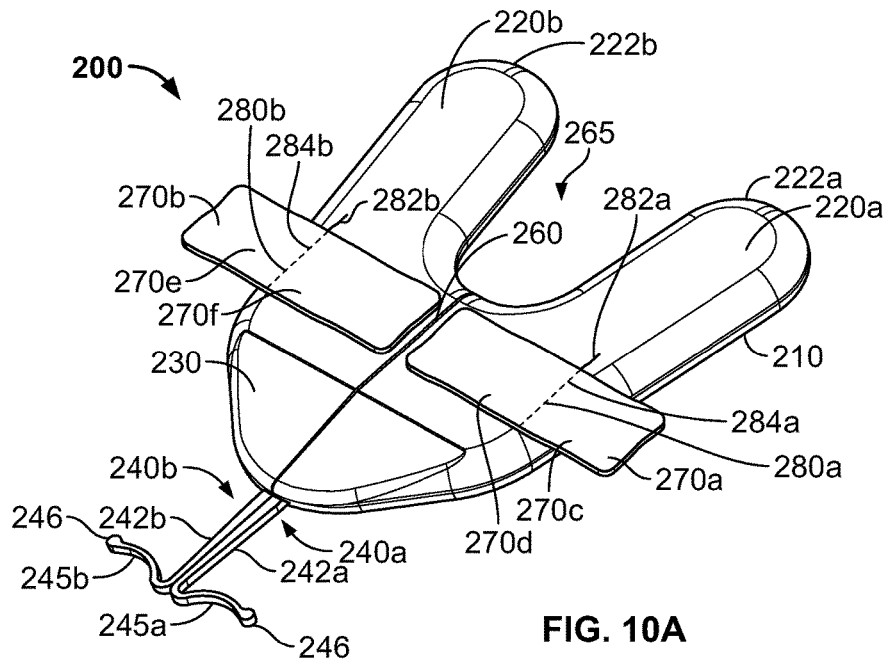
FIGS. 10A-C are perspective, side, and rear views, respectively, of the anchor device of FIG. 9.
Figure 10B:
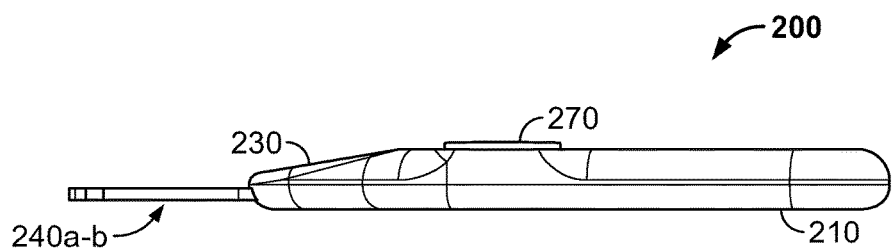

Referring now to FIGS. 10A-B, some embodiments of the anchor device 200 include the retainer body 210 and the anchors 240a-b, which are connected to and extend distally from the distal end of the retainer body 210. For example, the anchors 240a and 240b can be connected to the retainer body 210 using an over-molding process to secure the anchors 240a-b relative to the retainer body 210. It should also be understood that there exist many manufacturing processes that can secure the anchors 240a and 240b to the retainer body 210. In some embodiments, the retainer body 210 and the anchors 240a and 240b can be manufactured as a single, unitary piece.

Figure 11A:
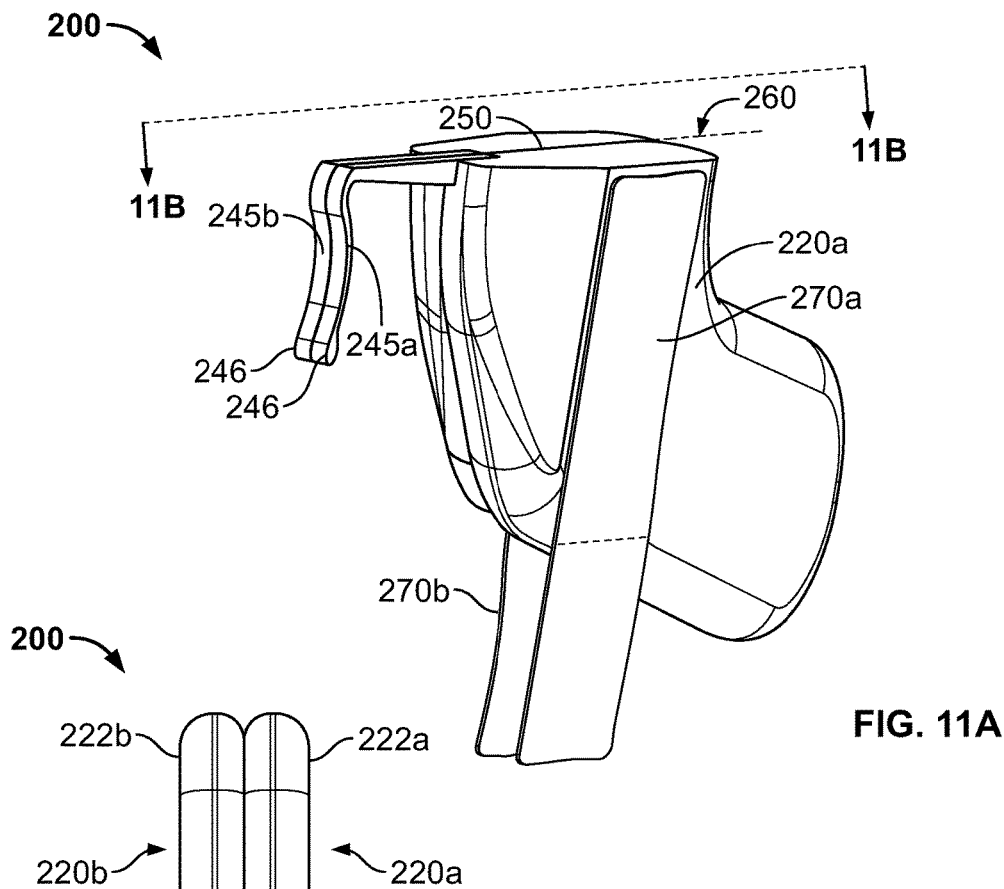
FIGS. 11A-B are perspective and top views, respectively, of the anchor device of FIG. 9 in a folded condition, in accordance with some embodiments.
Figure 11B:
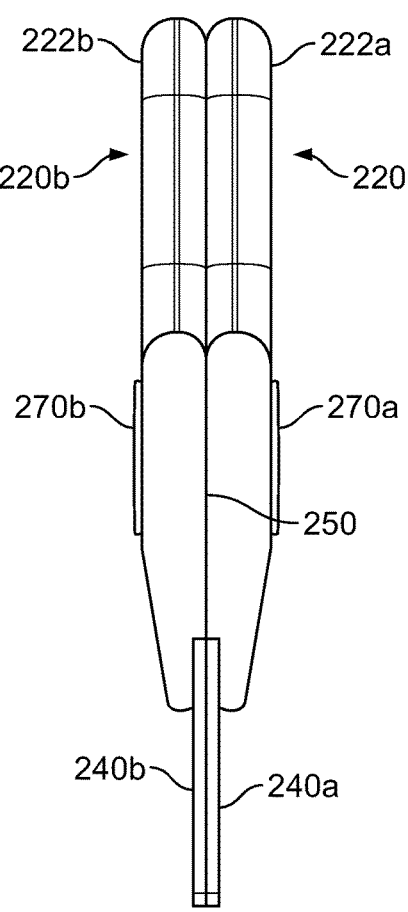

In particular embodiments, the anchor device 200 can be configured to be folded longitudinally about a longitudinal fold axis 260 (e.g., a longitudinally extending region configured for enabling the retainer body 210 to repeatedly adjust from a first position to a second, folded position as shown, for example, in FIGS. 11A-11B). Consequently, the retainer body 210 can be described as having a first retainer body portion 220a and a second retainer body portion 220b. In some embodiments, the first and second retainer body portions 220a-b can be substantially mirror images of each other. In alternative embodiments, the first and second portions of the anchor device 200 can be asymmetrical.

The composition and construction of the anchors 240a-b may be the same as that of anchors 140a-b, discussed with reference to FIGS. 1-8. For example, the anchors 240a-b may comprise a material that exhibits superelasticity. Moreover, each of the anchors 240a-b may be designed such that the tines 245a-b have an unstressed position wherein the tines 245a-b have a convex curvature with tine tips 246 that are bulbs. The composition of the retainer body 210 and the connection of the retainer body 210 to the anchors 240a-b may be the same as that of the retainer body 110 and the anchors 140a-b.

Figure 10C:
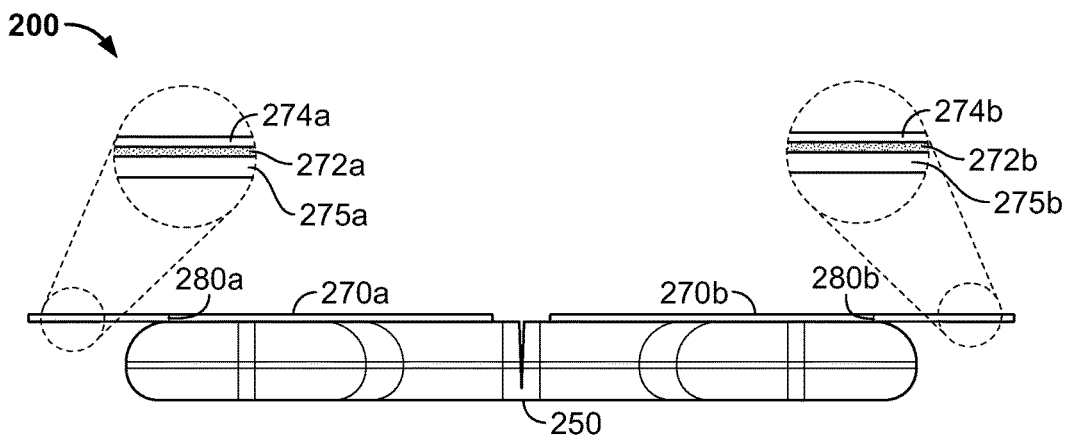

Still referring to FIGS. 10A-C, the retainer body 210 can include first and second retainer body portions 220a-b arranged on opposing sides of the longitudinal fold axis 260, left and right tabs 222a-b, and (optionally) a sloped nose region 230. The first and second retainer body portions 220*a-b* can be connected to each other at an elastically flexible web portion 150, which may be employed to define the fold axis 260.

Still referring to FIGS. 10A-C, the adhesive fabric strips 270*a-b* can be configured to provide an effective coupling interface with the catheter 202 or other medical instrument, while providing features that simplify the overall use of the medical device anchor system 204. For example, in this embodiment, the adhesive fabric strips 270*a-b* may provide the user with a simplified coupling technique for mating the anchor device 200 to the catheter 202, and may furthermore do so without the need for an attachable cap device or skin sutures. In the depicted example, the adhesive fabric strips 270*a-b* in general are sized and attached the retainer body 210, for example, so that the adhesive fabric strips 270*a-b* may be folded along fold axes 284*a-b* of the adhesive fabric strips 270*a-b*. The fold axes 284*a-b* of the adhesive fabric 270 may be offset from but parallel to the longitudinal fold axis 260. The tear strips 280 may be located along the fold axes 284*a-b*. The tear strips 280*a-b* of the adhesive fabric strips 270*a-b* can define borders between different regions of the adhesive fabric strips 270*a-b*. Consequently, adhesive fabric 270*a* can be described as having a first adhesive fabric portion 270*c* and a second adhesive fabric portion 270*d*, and the adhesive fabric 270*b* can be described as having a first adhesive fabric portion 270*e* and a second adhesive fabric portion 270*f*. The fold axes 284*a-b* may be defined along the tear strips 280*a-b*.

The adhesive and flexible characteristics of the adhesive fabric strips 270*a-b* enable a user to fold the first adhesive fabric portions 270*c* and 270*e* onto the top surfaces 29*a-b* of the wings 24*a-b*. In this manner, the first adhesive fabric portions 270*c* and 270*e* adhere to the top surfaces 29*a-b* of the wings 24*a-b* of the catheter 210. Furthermore, second adhesive fabric portions 270*d* and 270*f* may adhere to bottom surfaces 31*a-b* of the wings 24*a-b*. Thus, when securing the medical device 202 to the retainer body 210, the user can place the medical device 202 in contact with at least one of the second adhesive fabric portions 270*d* and 270*f*, and can thereafter fold the adhesive fabric strips 270*a-b* along the fold axes 284*a-b* (which may include a visual indicia of the fold axes 284*a-b*, such as solid or dotted lines imprinted on the adhesive fabric strips 270*a-*). During the folding, the user may press the first adhesive fabric portions 270*c* and 270*e* onto the top surfaces 29*a-b* of the wings 24*a-b*. The contact of the wings 24*a-b* with the adhesive fabric strips 270*a-b* may result in a snug coupling of the catheter 202 to the retainer body 210.

In the embodiment shown in FIG. 10B, the adhesive fabric strips 270*a-b* are bonded to outer surfaces of the retainer body 210, for example with a medical adhesive. In other embodiments (not shown), the adhesive fabric strips 270*a-b* are molded into the retainer body 210 at junctions, for example, slots in the retainer body 210 with an insert molding operation. The adhesive fabric strips 270*a-b* may be mechanically latched into junction 270. It should also be understood that there exist many manufacturing processes that can secure the adhesive fabric strips 270*a-b* to the retainer body 210.

As will be described further below in reference to FIG. 14, the flexibility of the wings 24*a-b* can allow some limited angular freedom of movement between the hub 42 and the anchor device 200, while generally restraining movement of the catheter 202 away from the skin penetration point 32. Further, the limited angular freedom of movement permits the hub 42 of the catheter 202 to be slightly titled relative to the anchor device 200, thereby permitting the hub 202 and the distal portion 48 of the medical instrument to more closely align with the skin penetration point 32 and reduce the stresses applied by the catheter 202 at the skin penetration point 32.

Still referring to FIGS. 10A-C, the anchor device 200 further includes first and second tabs 222*a-b*. The first and second tabs 222*a-b* are configured to simplify the act of manipulating and folding the anchor device 200. For example, as described further in reference to FIGS. 11A-B, the user can adjust the first and second tabs 222*a-b* in a pivoting motion toward one another, which readily enables the user to fold the anchor device 200 along the longitudinal fold axis 260. The first and second tabs 222*a-b* are also configured to provide a u-shaped cutout region 265 between the first and second tabs 222*a-b*. This u-shaped cutout region 265 can more readily provide visualization and access to the skin region under the retainer body 210 for inspection and cleaning of the skin 30 around the skin penetration point 32.

The anchor device 200 also includes a sloped nose region 230. The sloped nose region 230 can be a generally planar surface near the distal end of the retainer body 210 that is oriented at a different angle than the generally planar surfaces of the first and second retainer body portions 220*a-b*. The sloped nose region 230 can decline from the generally planar surfaces of the first and second retainer body portions 220*a-b* such that the nose region 230 slopes downward in a distal direction towards longitudinal shafts 242*a-b* of the anchors 240*a-b* (e.g., and thus downward to the skin penetration point 32 when the anchor tines 245*a-b* are deployed). As will be described further in reference to FIG. 14, the sloped nose region 230 can facilitate an orientation of the distal portion 48 of the catheter 202 that is directed toward the skin penetration point 32. In this manner, the stresses that can potentially be exerted on the skin 30 proximal to the skin penetration point 32 by the distal portion 48 of the catheter 202 can be reduced.

As shown in FIG. 10C, the flexible web portion 250 of the anchor device 200 can be positioned, for example, generally centrally between the first and second retainer body portions 220*a-b*. As previously described, the flexible web portion 250 can extend longitudinally from a distal face of the retainer body 210 to a proximal face of the retainer body 210, and can be used to define the fold axis 260 about which the first and second retainer body portions 220*a-b* are pivotable from the non-folded condition (FIG. 10A) to the folded condition (FIG. 11A). The left and right retainer body portions 220*a-b* can be connected to opposing sides of the flexible web portion 250. The flexible web portion 250 can comprise an elastically flexible biocompatible polymer material, as discussed with reference to FIG. 2C. The flexible web portion 250 can be biased to resiliently maintain the non-folded shape of the anchor device 200 as depicted in FIGS. 10A-10C. When the anchor device 200 is folded along the fold axis 260 due to a user's grasp (refer, for example to FIG. 4), the flexible web portion 250 can undergo elastic deformation such that flexible web potion 250 biases the anchor device 200 to return the non-folded condition (FIGS. 2A and 5) upon release from the user. In some embodiments, the adhesive fabric strips 270*a-b* comprise a single fabric that is joined across the fold axis 260. The single fabric may stretch and bias the anchor device 200 to the non-folded condition.

Referring now to FIGS. 11A-11B, in this example embodiment, the anchor device 200 may include features that allow the individual anchors 240*a-b* to be moved relative to each other so as to facilitate both insertion and removal of the anchor device 200 through the skin penetration point 32, for example, as discussed with reference to FIGS. 3A-3B in regard to anchor device 100 and individual anchors 140a-b.

Figure 12:
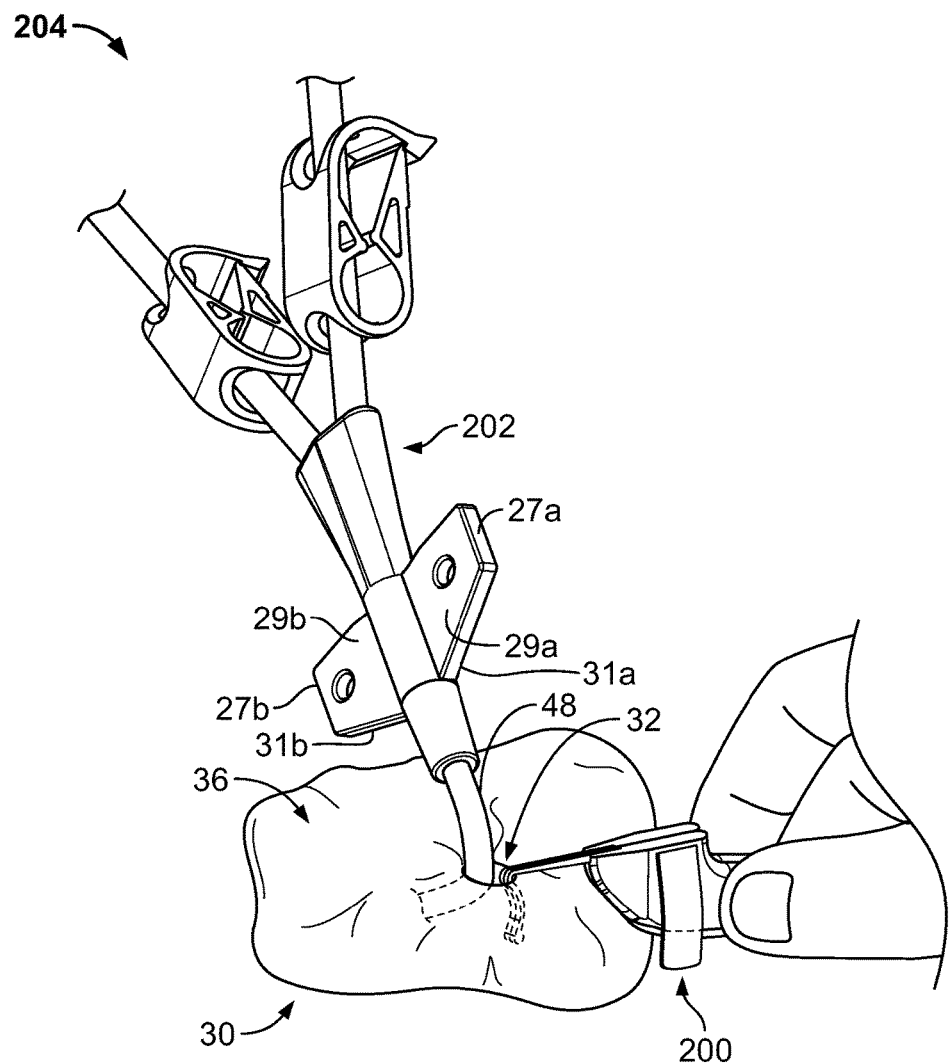
FIGS. 12-16 are perspective views of an anchor system, including the anchor device of FIG. 9, for use in securing the position of a medical instrument.
Figure 13:
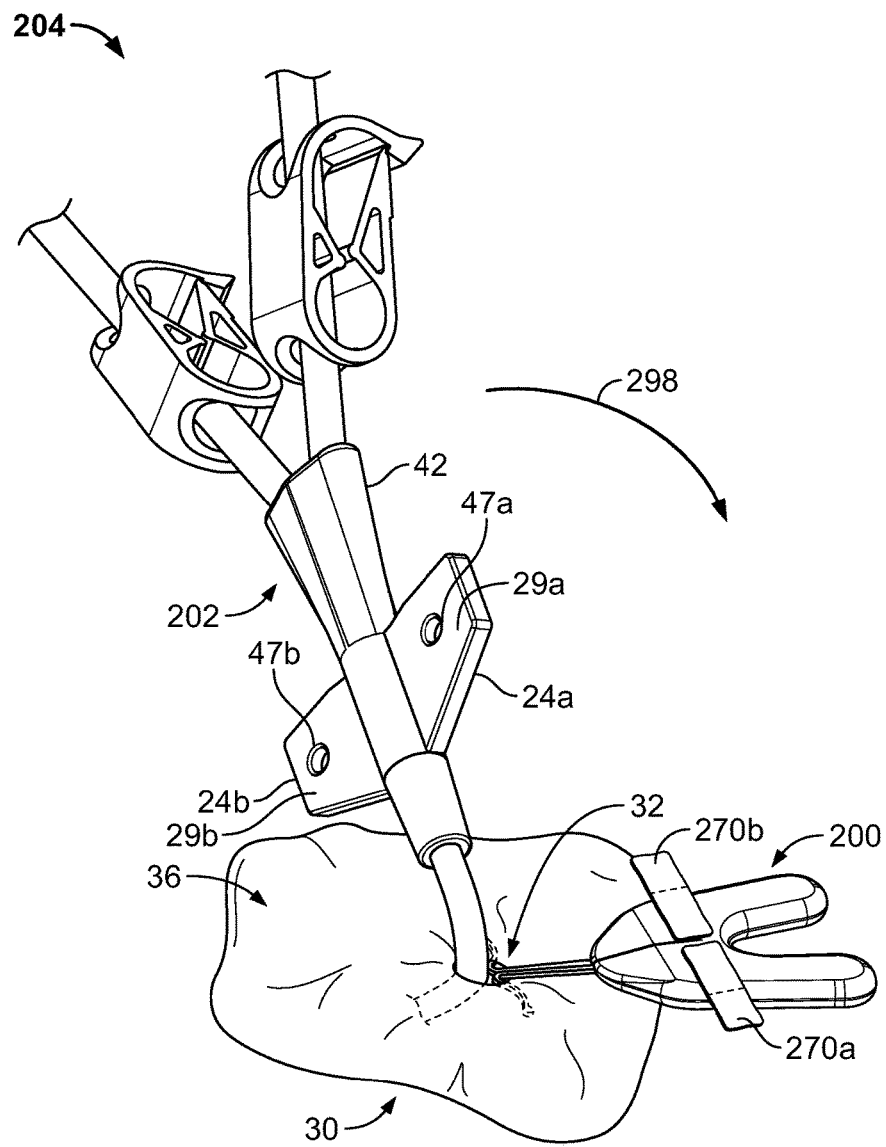

Referring now to FIGS. 12-13, in some embodiments, the catheter 202 can include a catheter to be inserted through the penetration point 32 of the skin 30 as part of a medical procedure. After placement of the catheter 202 through the penetration point 32 of the skin 30, the user can grasp the anchor device 200 in the folded condition and approach the penetration point 32 such that the free ends of the tines 245a-b are contemporaneously inserted through the penetration point 32 while the tines 245a-b are in a generally side-by-side condition (as depicted in FIG. 12). In particular embodiments, the subcutaneous tines 245a-b are inserted through the skin penetration point 32 while the user conveniently grasps the tabs 222a-b of the retainer body 210 of the anchor device 200 and applies an insertion force until the convexly curved body portions of the subcutaneous tines 245a-b are positioned below the surface of the skin 30 (while the remainder of the anchor device 200 resides external to the skin 30).

As the anchor device 200 is inserted through the penetration point 32, the tines 245a-b are maintained in a generally non-stressed configuration (e.g., a first shape or a steady-state shape) while passing the penetration point 32 in a manner that reduces the likelihood of trauma to the surrounding skin tissue 30. As the tines 245a-b are collectively advanced through the penetration point 32, the free ends of the tines 245a-b are moved beneath the dermal skin layers 36 of the skin 30.

When the tines 245a-b reach the subcutaneous region 34, the retainer body 210 can adjusted to the unfolded condition so that the tines 245a-b are shifted relative to one another, resulting in the tines 245a-b extending outwardly away from one another (as depicted in FIG. 13). During that process of unfolding the retainer body 210, each tine 245a-b may retain their generally non-stressed configuration (e.g., the first shape or the steady-state shape). Thus, the anchor device 200 can be installed in accordance with a technique that reduces or eliminates the need to shift the subcutaneous anchors tines 245a-b to or from a flexed or stressed configuration during the passage through the skin penetration point 32. As such, the subcutaneous anchors tines 245a-b need not undergo substantial flexing during installation or removal, and in some embodiments, the subcutaneous anchors tines 245a-b can comprise a generally less costly material (such as stainless steel or biocompatible polymers) rather than more costly materials required for superelastic flexing.

As previously described, the anchor device 200 can secure the catheter 202 relative to a skin penetration point 32. With the anchor device 200 positioned such that subcutaneous anchors tines 245a-b are in their deployed configuration, as shown in FIG. 13, the user may remove the releasable liners 274a-b of the adhesive fabric strips 270a-b, exposing the adhesive layers 274a-b. (Alternatively, the user may remove the releasable liners 274a-b before installation of the subcutaneous tines 245a-b into the subcutaneous region 34.) After the releasable liners 274a-b have been removed, the previously inserted catheter 202 can be placed in contact with the anchor device 200. As shown in FIG. 13, the directional arrow 298 depicts an example motion of manually positioning the catheter 202 in contact with the anchor device 200 to prepare for the coupling of the catheter 202 to the anchor device 200.

Figure 14:
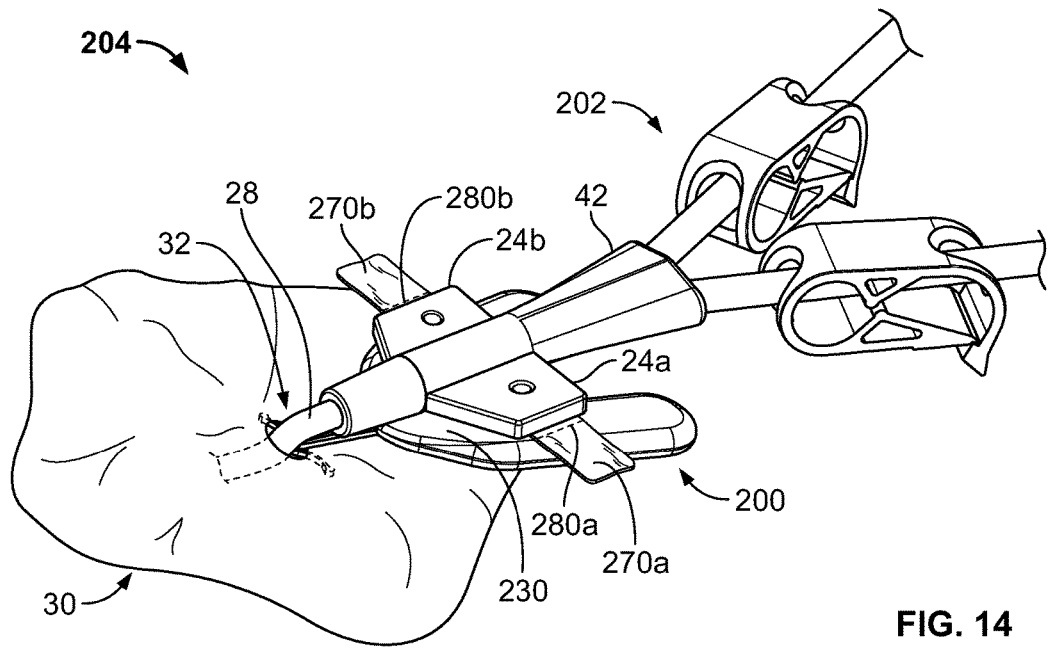

Referring now to FIG. 14, the hub 42 of the catheter 202 can be placed in contact with the anchor device 200 so that the wings 24a-b of the hub 42 are, for example, generally aligned with the corresponding adhesive fabric strips 270a-b. In doing so, the wings 24a-b are placed in contact with the adhesive layer 272 of corresponding adhesive fabric strip 270a-b, thereby temporarily retaining the catheter 202 is a position to receive the remaining portions of the adhesive fabric strips 270a-b over an upper side of the wings 24a-b. In order to adhesively couple the catheter 202 to the anchor device 202, the user may fold the adhesive fabric strips 270a-b (with the adhesive layer 272 exposed) along the fold axes 284a-b and onto the wings 24a-b, preferably aligning the tear strips 280a-b along the side surfaces 27a-b.

Figure 15:
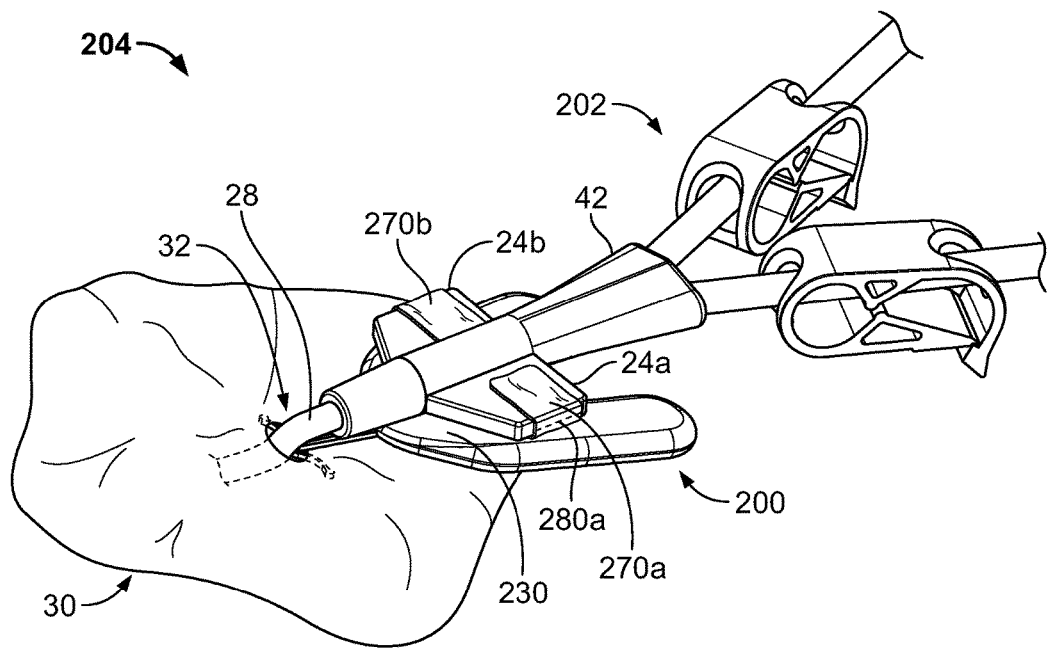

Referring now to FIG. 15, the medical device anchor system 204 of FIGS. 12-13 is adhesively coupled to the medical instrument 202. For example, the adhesive fabric strips 270a-b can be folded along the fold axes 284a-b and onto the top surfaces 29a-b. In the embodiment shown in FIG. 15, the first adhesive fabric portion 270c is in contact with the top surface 29a and the first adhesive fabric portion 270e is in contact with the top surface 29b. The second adhesive fabric portion 270d may be in contact with the bottom surface 31a and the second adhesive fabric portion 270e may be in contact with the bottom surface 31b. With the adhesive fabric strips 270a-b folded onto the wings 24a-b and adhesively bonded to the top surfaces 29a-b of the wings 24a-b, the catheter 202 is fixed to the anchor device 200.

As shown in FIG. 15, the anchor device 200 adhesively retains the medical instrument 202 (e.g., catheter) in an operative position relative to a portion of skin 30 (e.g., the skin penetration point 32). The medical instrument 202 is adhesively coupled to the anchor device 200, as described above. The anchor device 200, in turn, is coupled to the portion of skin 30, as described above. In such embodiments, the anchor device 200 can be secured to the patient without necessarily requiring sutures or adhesive tapes bonded to the skin 30. A distal portion 48 of the catheter 202 penetrates a skin penetration point 32 and distally extends into the subcutaneous layer 34. In this view, it can be seen that some embodiments of the system 204 can enable the distal end of the hub 42 to be positioned closely to the skin penetration point 32. Such a configuration provides a compact anchor system 204 that is convenient to install and maintain. This configuration can minimize the lengths of the tubing proximal to the patient, and reduce the need for securement of such tubing or other portions of the medical instrument 202 to the patient using tapes, adhesive dressings, and the like.

It can also be seen in FIG. 15 that the hub 42 of the catheter 202 may optionally inclined at an angle in relation to the skin surface 30. Such an orientation between the hub 42 and the skin 30 may, in some circumstances, reduce the stresses applied to the skin penetration point 32 of the patient by the distal portion 48 of the catheter 202. In particular, the example orientation depicted in FIG. 15 enables the distal portion 48 to be inclined at an angle in relation to the skin surface 30 which can thereby reduce the need for the distal portion 48 of the catheter 202 to have a significant bend at the skin penetration point.

Figure 16:
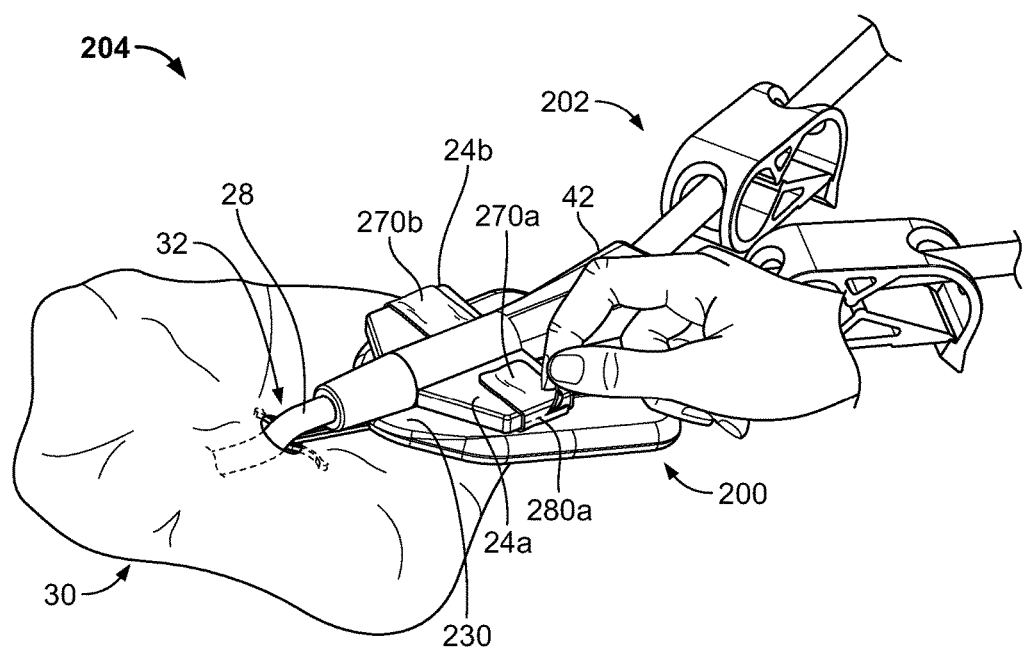

FIG. 16 illustrates an example of removing of the catheter 202 from the anchor device 200. In this example, the user has grasped the protruding portions 282a of the tear strips 280a, and pulled the protruding portion 282a away from the retainer body 210, ripping the adhesive fabrics 270a at the location of the tear strip 180a and permitting removal of the medical device 202 due to separation in the adhesive fabrics 270a. FIG. 16 shows the system 204 during removal of the tear strips 280a and ripping of the adhesive fabrics 270a, but it should be understood that both tear strips 280*a-b* may be completely removed from the adhesive fabric strips 270*a-b*, resulting in a complete separation of both adhesive fabric strips 270*a-b*, for example, along the fold axes 284*a-b*. It is after the complete separation of the adhesive fabric strips 270*a-b* that the catheter 202 may be removed from contact with the retainer body 210. In some examples, the catheter 202 is removed from contact with both the retainer body 210 and the subcutaneous layer 34 before the subcutaneous tines 245*a-b* are removed from the subcutaneous layer 34.

In some embodiments, some components of the system 204 can be provided in a sterilized kit that pairs a particular type of catheter 202 or other medical instrument with a corresponding anchor device 200. The particular type of catheter 202 or other medical instrument in the kit is compatible for adhesively mating with the anchor device 200 in the kit. Each kit can include one or more anchor devices 200 and the particular type of catheter 202 or other medical instrument enclosed within a flexible packaging material, which preferably includes indicators that identify the type of catheter 202 or other medical instrument that is provided along with instructions for deploying and removing the anchor device 200. The kit may include a one-to-one ratio for the quantity of anchor devices 200 to the quantity of catheters 202. In other embodiments, the kit may include multiple anchor devices 200 (e.g., having differently sized or shaped tines 245*a-b*) for each catheter 202 contained therein.

Alternatively, in some embodiments, the anchor device 200 can be provided in individual, sterilized packets so that a user can readily open such a packet and access the selected anchor device prior to insertion into the skin penetration point. Such individual packets can include a single anchor device enclosed within a flexible packaging material, which preferably includes indicators that identify the types of catheters or other medical instruments that are compatible for adhesively mating with the anchor device 200. As such, a user can readily select one of the packets for use after the type of catheter or medical instrument is selected for a particular patient.

Figure 17A:
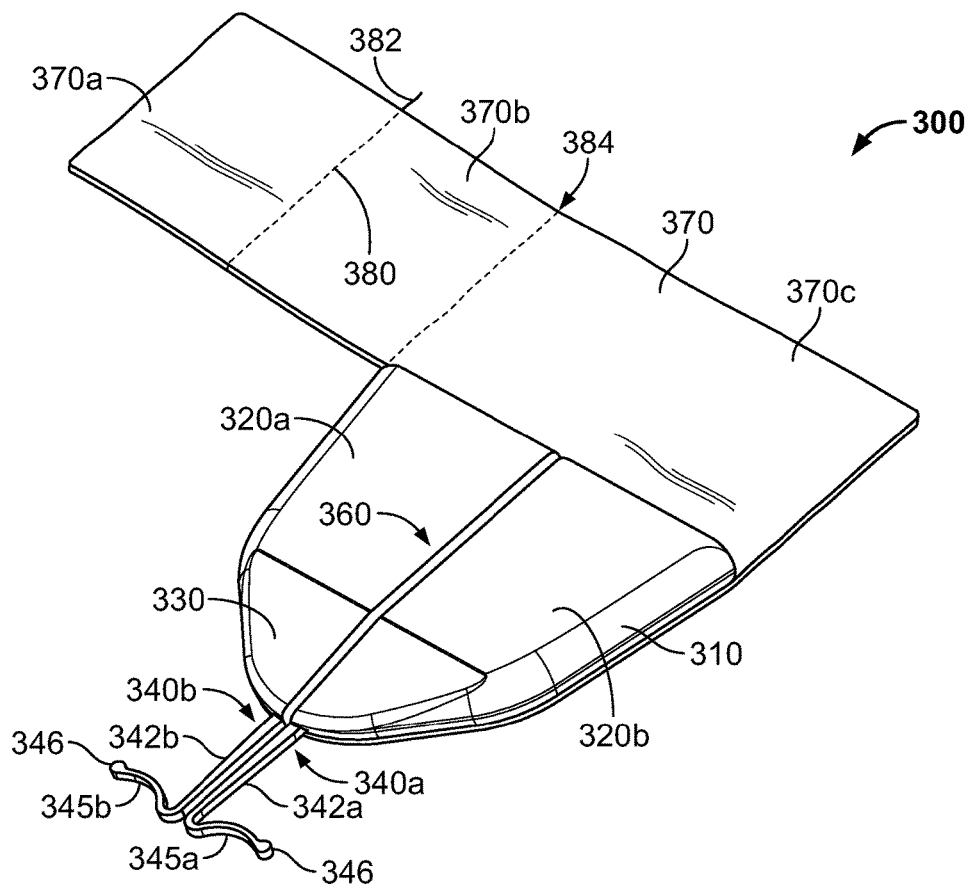
FIGS. 17A-17B are perspective and side views, respectively, of an anchor device in accordance with some alternative embodiments.
Figure 17B:
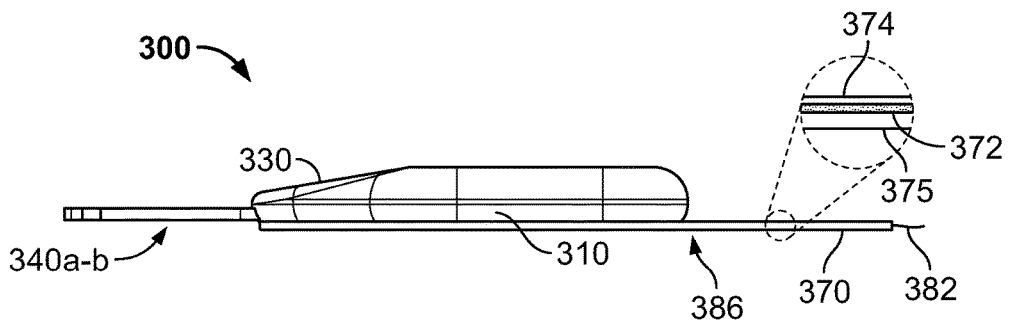

Referring to now FIGS. 17A-B, some embodiments of the medical device anchor system include an anchor device 300 that adhesively retains a medical instrument (e.g., a catheter 102 as shown in FIG. 1, or the like) in an operative position relative to a portion of skin. Similar to the embodiments previously described in connection with FIGS. 1-8, the anchor device 300 can act as an intermediary member to cause the retention of the medical instrument in a desired position with respect to the skin 30. In this example, the anchor device 300 can generally include a retainer body 310 (including first and second portions 320*a-b*), a flexible adhesive web 370, and one or more anchors 340*a-b*. The anchor device 300 is similar to the embodiments previously described in connection with FIGS. 1-8, except that flexible adhesive web 370 is disposed along an underside of the retainer body 310. For example, the retainer body 310 can include two separate portions 320*a-b* that are affixed to a designated region of the flexible adhesive web 370 (refer to FIG. 17A), and the longitudinal fold region 360 is defined by a small portion of the flexible adhesive web 370 positioned between opposing edges of the spate body portions 320*a-b*. In this example, the flexible adhesive web 370 can serve both as the longitudinal hinge portion (e.g., that defines a longitudinal fold line for the retainer body 310) and as the securement structure for the medical instrument. Optionally, during manufacture of the anchor device 300, the two individual body portions 320*a-b* (each having a corresponding anchor 340*a-b* extending distally therefrom) can be bonded to an exposed region of an adhesive layer of the underlying flexible adhesive web 370. The proximal regions 370*a-b* of the flexible adhesive web 370 may be equipped with a release liner 374 so as to preserve the portion of the adhesive layer 372 until the proximal regions 370*a-b* are used to adhere to the catheter or other medical instrument.

Similar to the anchors 140*a-b* previously described in connection with FIGS. 1-8, the anchors 340*a-b* extend distally from a distal end of the retainer body 310 for deployment through a skin penetration point and into a subcutaneous layer, so as to releasably retain the anchor device 300 with respect to the skin. As such, the anchor device 300 can include the one or more anchors 340*a* and 340*b* that extend distally from the retainer body 310 so as to penetrate through the same skin penetration point while the retainer body 310 and the flexible adhesive web 370 remain external to the skin penetration point. Also similar to the anchors 140*a-b* previously described in connection with FIGS. 1-8, the anchors 340*a-b* can include longitudinal shaft portions 342*a-b* that extend distally to corresponding subcutaneous tines 345*a-b*. After insertion of the tines 345*a-b*, the tines 345*a-b*, reside in the subcutaneous region so as to secure the position of the anchor device 300—and the medical instrument retained thereto—relative to the penetration point. When the tines 345*a-b* are deployed in the subcutaneous region, the anchor device 300 can be secured to the patient without the retainer body 310 penetrating through the dermal layers of the patient, and without necessarily requiring sutures or adhesive tapes bonded to the skin. As previously described, the anchor device 300 can be installed into the skin penetration point in accordance with a technique that reduces or eliminates the need to shift the subcutaneous anchors tines 345*a-b* of the anchors 340*a-b* to or from a flexed or stressed configuration. As such, the anchor tines 345*a-b* may not necessarily undergo substantial flexing during installation or removal. In these circumstances, the subcutaneous anchors may be both installed and removed from the skin penetration point advantageously without the need for an external actuator handle or delivery device to deploy the subcutaneous tines 345*a-b*.

Still referring to FIGS. 17A-B, after installation of the subcutaneous anchor tines 345*a-b* into the subcutaneous layer, the retainer body 310 and the flexible adhesive web 370 can receive the catheter or other medical instrument. For the flexible adhesive web 370 to receive the catheter, a user may have removed releasable liner 374 from the flexible adhesive web 370 to expose the adhesive layer 372. The catheter may be placed in contact with the exposed flexible adhesive web 370, and a user may fold the adhesive portions 370*a-b* (e.g., along the fold axis 384) over the catheter and into engagement with the remaining portion 370*c*.

Similar to the embodiments previously described in connection with FIGS. 1-8, the flexible adhesive web 370 may include a tear strip 380 that extends in a generally longitudinal direction (e.g., generally parallel to the longitudinal fold region 360 of the retainer body 310). The flexible adhesive web 370 may be adapted such that pulling the tear strip 380 results in the flexible adhesive web 370 separating along an installation of the tear strip 380 in the flexible adhesive web 370. The tear strip 380 may be manufactured with sufficient tensile strength to remain intact as the user pulls the tear strip 380 away from the flexible adhesive web 370, and as the flexible adhesive web 370 is ripped into two portions through force applied to the flexible adhesive web 370 by the tear strip 380. In some embodiments, the tear strip 380 may include a protruding portion 382 that is adapted to be grasped by the user with an instrument or between the user's fingers. Thus, after adhesive coupling of the catheter to the anchor device 300, the catheter may be removed in a straightforward manner from contact with the anchor device 300 and subcutaneous region before the tines 345a-b are removed from the subcutaneous region.

The flexible substrate 375 of the flexible adhesive web 370 can be manufactured from a flexible material such as a textile mesh, a polymer mesh, a polymer sheet, a flat web of polymer foam material, or a metallic foil. Preferably, the flexibile substrate 375 is selected with the material and thickness sufficient to bias the retainer body 310 to the deployed configuration (as shown in FIG. 17A) after being temporarily adjusted to a folded condition (e.g., fold about the longitudinal fold region 360). The adhesive layer 372 may comprise an adhesive, for example, a suitable medical adhesive. In some examples, a medical adhesive that is robust to cleaning agents and that provides a permanent hold may be employed as the adhesive layer 372. The releasable liner 374 may be formed of a polymer sheet or a wax paper, for example.

A number of embodiments of the invention have been described. Nevertheless, it will be understood that various modifications may be made without departing from the scope of the invention. Accordingly, other embodiments are within the scope of the following claims.

What is claimed is:

1. An anchor device for securing the position of a medical instrument, the anchor device comprising:
   a retainer body comprising a first body portion and a second body portion;
   one or more flexible adhesive strips mounted to the retainer body and being configured to adhesively attach with one or more corresponding exterior surfaces of the medical instrument; and
   first and second anchors that extend distally from a distal end of the retainer body, each anchor comprising a flexible tine that is deployable in a subcutaneous region to secure the retainer body relative to a penetration point, the first anchor being coupled to the first body portion and the second anchor being coupled to the second body portion;
   wherein the first body portion of the retainer body is movable relative to the second body portion about a longitudinal fold axis while the first and second body portions are coupled so that the first and second anchors are adjustable from a first configuration in which the flexible tines extend outwardly away from one another to a second configuration in which the flexible tines extend generally in the same direction; and
   wherein the one more flexible adhesive strips comprise a first adhesive strip configured to define an adhesive strip fold axis, the first adhesive strip foldable upon itself about the adhesive strip fold axis and around an exterior surface of the medical instrument, and wherein the adhesive strip fold axis is substantially parallel to and offset from the longitudinal fold axis of the retainer body.

2. The anchor device of claim 1 wherein the one or more flexible adhesive strips has a lateral width extending generally perpendicular to the longitudinal fold axis and a longitudinal length extending generally parallel to the longitudinal fold axis, wherein the lateral width of each respective flexible adhesive strip is substantially greater than the longitudinal length of the respective flexible adhesive strip.

3. The anchor device of claim 1, wherein the retainer body further comprises a sloped nose region that has a generally planar upper surface that is oriented at a decline angle extending distally from the first and second body portions.

4. The anchor device of claim 1, wherein the longitudinal fold axis is defined by a flexible web portion positioned generally centrally between the first and second body portions and extending longitudinally from the distal end of the retainer body to a proximal face of the retainer body.

5. The anchor device of claim 4, wherein the first body portion is hingedly movable relative to the second body portion about the longitudinal fold axis to adjust the first and second anchors between the first and second configurations.

6. The anchor device of claim 1, wherein the one or more flexible adhesive strips each comprise a flexible substrate carrying an adhesive layer along a major surface thereof and a releasable liner over the adhesive layer.

7. The anchor device of claim 6, wherein the flexible substrate comprises at least one of a fabric mesh material, a polymer mesh material, and a polymer sheet material.

8. The anchor device of claim 7, wherein the releasable liner comprises at least one of a polymer sheet material and wax paper material.

9. A system for securing the position of a medical instrument, the system comprising:
   a medical instrument comprising a distal portion configured to extend through a skin penetration point and into a body, and an external portion configured to reside outside the body when the distal portion extends through the skin penetration point; and
   an anchor device comprising;
   a retainer body comprising a first body portion that is coupled to a second body portion;
   one or more flexible adhesive strips mounted to the retainer body and being configured to adhesively attach with one or more surfaces of the external portion of the medical instrument; and
   first and second anchors that extend distally from a distal end of the retainer body, each anchor comprising a flexible tine that is deployable through the skin penetration point occupied by the medical instrument and into a subcutaneous region to secure the retainer body relative to the skin penetration point, the first anchor being coupled to the first body portion and the second anchor being coupled to the second body portion;
   wherein the first body portion of the retainer body is pivotable relative to the second body portion about a longitudinal fold axis while the first and second body portions are pivotably coupled so that the first and second anchors are adjustable from one another from a first configuration to a second configuration in which the flexible tines extend generally in the same direction; and
   wherein the one more flexible adhesive strips comprise a first adhesive strip configured to define an adhesive strip fold axis, the first adhesive strip foldable upon itself about the adhesive strip fold axis and around an exterior surface of the medical instrument, and wherein the adhesive strip fold axis is substantially parallel to and offset from the longitudinal fold axis.

10. The system of claim 9, wherein the retainer body further comprises a sloped nose region that has a generally planar upper surface that is oriented at a decline angle extending distally from the first and second body portions.

11. The system of claim 9, wherein the one or more flexible adhesive strips each have a lateral width extending generally perpendicular to the longitudinal fold axis and a longitudinal length extending generally parallel to the longitudinal fold axis, wherein the lateral width of each width of each respective flexible adhesive strip is substantially greater than the longitudinal length of the respective flexible adhesive strip.

12. The system of claim 9, wherein at least one of the one or more flexible strips comprises a tear strip that extends generally parallel to the longitudinal fold axis of the retainer body configured to separate the flexible strip into multiple portions.

13. The system of claim 9, wherein the longitudinal fold axis is defined by a flexible web portion positioned generally centrally between the first and second body portions and extending longitudinally from the distal end of the retainer body to a proximal face of the retainer body.

14. The system of claim 9, wherein the medical instrument comprises a catheter, and wherein the one or more flexible adhesive strips comprises an adhesive layer configured to bond with the one or more surfaces of the external portion of the catheter.

15. The system of claim 14, wherein the one or more flexible adhesive strips comprise a flexible substrate carrying an adhesive layer along a major surface thereof and a releasable liner over the adhesive layer.

16. The system of claim 15, wherein the flexible substrate comprises at least one of a fabric mesh material, a polymer mesh material, and a polymer sheet material.

17. The system of claim 16, wherein the releasable liner comprises at least one of a polymer sheet material and wax paper material.

18. A system for securing the position of a medical instrument, the system comprising:
 a medical instrument comprising a distal portion configured to extend through a skin penetration point and into a body, and an external portion configured to reside outside the body when the distal portion extends through the skin penetration point; and
 an anchor device comprising;
  a retainer body comprising a first body portion that is coupled to a second body portion;
  one or more flexible adhesive strips mounted to the retainer body and being configured to adhesively attach with one or more surfaces of the external portion of the medical instrument; and
  first and second anchors that extend distally from a distal end of the retainer body, each anchor comprising a flexible tine that is deployable through the skin penetration point occupied by the medical instrument and into a subcutaneous region to secure the retainer body relative to the skin penetration point, the first anchor being coupled to the first body portion and the second anchor being coupled to the second body portion;
 wherein the first body portion of the retainer body is pivotable relative to the second body portion about a longitudinal fold axis while the first and second body portions are pivotably coupled so that the first and second anchors are adjustable from one another from a first configuration to a second configuration in which the flexible tines extend generally in the same direction; and
 wherein the one more flexible adhesive strips comprise a first adhesive strip configured to define an adhesive strip fold axis, the first adhesive strip foldable upon itself about the adhesive strip fold axis and around an exterior surface of the medical instrument,
 wherein at least one of the one or more flexible strips comprises a tear strip that extends generally parallel to the longitudinal fold axis of the retainer body configured to separate the flexible strip into multiple portions,
 wherein the medical instrument comprises a catheter, and wherein the one or more flexible adhesive strips comprises an adhesive layer configured to bond with the one or more surfaces of the external portion of the catheter, and wherein the tear strip is substantially aligned with the catheter when the adhesive layer is bonded to the catheter.

19. The system of claim 18, wherein the one or more flexible adhesive strips comprise a flexible substrate carrying the adhesive layer along a major surface thereof and a releasable liner over the adhesive layer.

20. The system of claim 18, wherein the retainer body further comprises a sloped nose region that has a generally planar upper surface that is oriented at a decline angle extending distally from the first and second body portions.

* * * * *